United States Patent
Reiche et al.

(10) Patent No.: US 12,357,269 B2
(45) Date of Patent: *Jul. 15, 2025

(54) IMPLANTABLE AND BIODEGRADABLE SMART HYDROGEL MICROMECHANICAL RESONATORS WITH ULTRASOUND READOUT FOR BIOMEDICAL SENSING

(71) Applicant: UNIVERSITY OF UTAH RESEARCH FOUNDATION, Salt Lake City, UT (US)

(72) Inventors: Christopher F. Reiche, Salt Lake City, UT (US); Florian Solzbacher, Salt Lake city, UT (US); Navid Farhoudi, Salt Lake City, UT (US); Steven M. Blair, Salt Lake City, UT (US); Jules J. Magda, Salt Lake City, UT (US); Lars B. Laurentius, Cottonwood Heights, UT (US); Prattay Deepta Kairy, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/621,918

(22) Filed: Mar. 29, 2024

(65) Prior Publication Data

US 2024/0260935 A1    Aug. 8, 2024

Related U.S. Application Data

(63) Continuation of application No. 17/315,039, filed on May 7, 2021, now Pat. No. 11,980,498, which is a (Continued)

(51) Int. Cl.
*A61B 8/00* (2006.01)
*G10K 11/04* (2006.01)

(52) U.S. Cl.
CPC .......... *A61B 8/4272* (2013.01); *A61B 8/4483* (2013.01); *A61B 8/5207* (2013.01);
(Continued)

(58) Field of Classification Search
CPC ... A61B 8/4772; A61B 8/4483; A61B 8/5207; A61B 2562/0204; A61B 2562/028
See application file for complete search history.

(56) References Cited

U.S. PATENT DOCUMENTS

| | | |
|---|---|---|
| 11,445,997 B2 | 9/2022 | Avula et al. |
| 2002/0042065 A1 | 4/2002 | Han et al. |

(Continued)

FOREIGN PATENT DOCUMENTS

| | | |
|---|---|---|
| WO | 2018/045333 A1 | 3/2018 |
| WO | 2018/231875 A1 | 12/2018 |

OTHER PUBLICATIONS

Advisory Action (PTOL-303) Mailed on Apr. 15, 2022 for U.S. Appl. No. 16/330,048 3 pages.
(Continued)

*Primary Examiner* — Joel F Brutus
(74) *Attorney, Agent, or Firm* — Workman Nydegger

(57) ABSTRACT

Systems and methods for measuring changes in smart hydrogel microresonator structures positioned in an in vivo or other environment, having an acoustic resonance frequency in an ultrasound range. The system includes a smart hydrogel microresonator structure positioned within the environment configured to exhibit a change in resonance frequency in response to interaction with one or more predefined analytes in the environment. The system includes an ultrasound transducer for querying the smart hydrogel microresonator structure at or near its resonance frequency. The system also includes a computer system configured to receive ultrasound data as provided by query of the smart (Continued)

Smart hydrogel scaffold (implantable size) with smart hydrogel microresonator particles trapped in cavities hydrogel microresonator structure and to determine changes in resonance frequency, amplitude or intensity of the ultrasound query wave, or mean grayscale value (MGV) associated with the ultrasound data of the smart hydrogel microresonator structure due to the change in resonance frequency. Such change can be correlated to concentration of the analyte.

22 Claims, 15 Drawing Sheets

Related U.S. Application Data continuation-in-part of application No. 16/330,048, filed as application No. PCT/US2017/049944 on Sep. 1, 2017, now Pat. No. 11,445,997.

(60) Provisional application No. 63/022,098, filed on May 8, 2020, provisional application No. 62/552,623, filed on Aug. 31, 2017, provisional application No. 62/518,491, filed on Jun. 12, 2017, provisional application No. 62/518,456, filed on Jun. 12, 2017, provisional application No. 62/435,491, filed on Dec. 16, 2016, provisional application No. 62/435,537, filed on Dec. 16, 2016, provisional application No. 62/383,344, filed on Sep. 2, 2016.

(52) U.S. Cl.
CPC ...... *G10K 11/04* (2013.01); *A61B 2562/0204* (2013.01); *A61B 2562/028* (2013.01)

(56) References Cited

U.S. PATENT DOCUMENTS

| 2003/0100822 | A1* | 5/2003 | Lew ............... A61B 5/14865 |
| | | | 600/365 |
| 2005/0074406 | A1 | 4/2005 | Couvillon et al. |
| 2007/0239016 | A1 | 10/2007 | Fisher |
| 2009/0170124 | A1 | 7/2009 | Campbell |
| 2013/0245402 | A1 | 9/2013 | Ziaie et al. |
| 2013/0338503 | A1 | 12/2013 | Cohen et al. |
| 2014/0182361 | A1 | 7/2014 | Bargatin et al. |
| 2014/0271767 | A1 | 9/2014 | Askari et al. |
| 2015/0087945 | A1 | 3/2015 | Ziaie et al. |
| 2015/0087978 | A1 | 3/2015 | Wada et al. |
| 2016/0015323 | A1 | 1/2016 | Tathireddy et al. |
| 2016/0033389 | A1 | 2/2016 | Serpe |
| 2019/0192113 | A1 | 6/2019 | Christensen et al. |
| 2020/0093408 | A1 | 3/2020 | Solzbacker et al. |
| 2021/0267573 | A1 | 9/2021 | Reiche et al. |
| 2021/0338195 | A1 | 11/2021 | Reiche et al. |

OTHER PUBLICATIONS

Final Rejection Mailed on Nov. 10, 2021 for U.S. Appl. No. 16/330,048, 29 page(s).
International Search Report and Written Opinion issued in PCT/US2018/037166 mailed Sep. 11, 2018.
International Search Report and Written Opinion, PCT/US2017/049944, United States International Search Authority, Completed Oct. 20, 2017.
Millet et al., "Characterization of Mass and Swelling of Hydrogel Microstructures using MEMS Resonant Mass Sensor Arrays", Nano, Micro, Small vol. 8 iss. 16, (Aug. 20, 2012), p. 2555-2562 (Year: 2012).
Non-Final Office Action received for U.S. Appl. No. 16/330,048, mailed on Jul. 20, 2021, 21 pages.
Notice of Allowance and Fees Due (PTOL-85) Mailed on May 12, 2022 for U.S. Appl. No. 16/330,048, 8 page(s).
Office Action received for European Patent Application No. 16/330,048, mailed on Mar. 4, 2022, 3 pages.
Park J H et al: "A wireless chemical sensing scheme using ultrasonic imaging of microbubble embedded hydrogel", 2015 Transducers—2015 18th International Conference on Solid-State Sensors, Actuators and Microsystems (Transducers), IEEE, Jun. 21, 2015 (Jun. 21, 2015), pp. 2220-2223, XP033189786, DOI: 10.1109/Transducers.2015.7181402 [retrieved on Aug. 5, 2015].
Rey et al., "Monitoring swelling and deswelling of thin polymer films by microcantilever sensors", Sensors and Actuators B: Chemical, (2014), p. 602-610 (Year: 2014).
Ritcher et al., "Review on Hydrogel-based pH Sensors and Microsensors", Sensors 2008, vol. 8 No. 1, p. 561-581 (Year: 2008).
Sannino et al., "Spin coating cellulose derivatives on quartz crystal microbalance plates to obtain hydrogel-based fast sensors and actuators", Journal of Applied Polymer Science vol. 106 iss. 5, (Dec. 5, 2007), p. 3040-3050 (Year: 2007).
Tavakoli et al. "Hydrogel Based Sensors for Biomedical Applications: An Updated Review" Polymers 2017, 9, 364.

\* cited by examiner

Smart hydrogel microresonator particles

Smart hydrogel scaffold (swollen) with cavities

Smart hydrogel scaffold (implantable size) with smart hydrogel microresonator particles trapped in cavities

IMPLANTABLE AND BIODEGRADABLE SMART HYDROGEL MICROMECHANICAL RESONATORS WITH ULTRASOUND READOUT FOR BIOMEDICAL SENSING

CROSS-REFERENCE TO RELATED APPLICATIONS

This application is a continuation under 35 U.S.C. 120 of U.S. patent application Ser. No. 17/315,039, filed May 7, 2021 and titled "IMPLANTABLE AND BIODEGRADABLE SMART HYDROGEL MICROMECHANICAL RESONATORS WITH ULTRASOUND READOUT FOR BIOMEDICAL SENSING", which claims the benefit under 35 U.S.C. 119(e) of U.S. Provisional Patent Application Ser. No. 63/022,098, filed May 8, 2020 and titled "SMART HYDROGEL MICROMECHANICAL RESONATORS WITH ULTRASOUND READOUT FOR BIOMEDICAL SENSING", each of which is herein incorporated by reference in its entirety.

Application Ser. No. 17/315,039 is also a continuation-in-part under 35 U.S.C. 120 of U.S. patent application Ser. No. 16/330,048, filed Mar. 1, 2019 and titled "ULTRASOUND IMAGING OF BIOMARKER SENSITIVE HYDROGELS, which is a U.S. National Stage Application under 35 U.S.C. 371 of PCT Application Serial No. PCT/US17/49944 filed Sep. 1, 2017, titled "ULTRASOUND IMAGING OF BIOMARKER SENSITIVE HYDROGELS", which claims the benefit of (1) U.S. Provisional Patent Application No. 62/552,623, filed Aug. 31, 2017 and titled "HYDROGEL ULTRASOUND RESONATORS FOR BIOMARKER SENSING." (2) U.S. Provisional Patent Application No. 62/518,491, filed Jun. 12, 2017 and titled "METHODS TO DETECT VOLUME CHANGES OF HYDROGELS USING ULTRASOUND," (3) U.S. Provisional Patent Application No. 62/518,456, filed Jun. 12, 2017 and titled "METHODS TO DETECT VOLUME CHANGES OF HYDROGELS USING ULTRASOUND," (4) U.S. Provisional Patent Application No. 62/435,537, filed Dec. 16, 2016 and titled "NOVEL METHODS TO DETECT VOLUME CHANGES OF HYDROGELS USING ULTRASOUND," (5) U.S. Provisional Patent Application No. 62/435,491, filed Dec. 16, 2016 and titled "HYDROGEL ULTRASOUND RESONATORS FOR BIOMARKER SENSING," and (6) U.S. Provisional Patent Application Ser. No. 62/383,344, filed Sep. 2, 2016 and titled "ULTRASOUND BASED TRANSDUCER MECHANISM FOR HYDROGEL SENSORS," Each of the aforementioned is incorporated herein by reference in its entirety.

STATEMENT REGARDING FEDERALLY SPONSORED RESEARCH OR DEVELOPMENT

This invention was made with government support under grant no. GM130241 awarded by the National Institutes of Health. The government has certain rights in the invention.

BACKGROUND

Technical Field

This disclosure generally relates to methods and systems for detecting a target analyte in a given environment. More specifically, in one particular application, the present disclosure relates to using ultrasound to detect the state of biomarker sensitive hydrogels in vivo. Which such in vivo medical use is one particular contemplated use, the present disclosure has broader application so as to be applicable in other fields, e.g., to detect and/or measure the amount of a given target analyte in any of a wide variety of environments (e.g., using ultrasound to "read" the hydrogel in the given environment).

Related Technology

Advances in computing technology have resulted in a concomitant advance in medical device technologies, including within the field of diagnostic and interventional medicine. Particularly, the past century has demonstrated significant advances in medical imaging devices. Such advances have been hallmarked by the advent of radiologic devices such as computed tomography, magnetic resonance imaging, ultrasound, and other imaging devices that allow for the non-invasive viewing and exploration of internal structures of the body. These devices are often used with interventional radiology and minimally invasive surgeries as well, providing image guidance for any of a plethora of medical devices operated by a physician.

The non-invasive nature of medical imaging devices provide certain advantages, but they also have their limitations. Magnetic resonance imaging, for example, requires a patient to hold completely still in a confined area while the overly large, loud, and expensive imaging machine obtains imaging data. Other medical imaging devices, such as those utilized for medical ultrasound, are less expensive but often cannot provide high-resolution images of deep tissue sites.

Further, medical imaging devices are limited by the kind of information reported. Ultrasound, for example, generally relies on sonically reflective surfaces to produce an image and provides little information outside of the image data that can be derived from sonically reflective surfaces within the body. In some instances, ultrasound can be used to detect and monitor blood flow and heart rate, but ultrasound lacks the resolving power to identify the presence or absence—let alone the concentration—of biomarkers within the body. The other medical imaging techniques and devices available similarly lack the ability to identify biomarkers within the body, and while the medical imaging devices developed over the past century have allowed physicians and clinicians to better document, treat, and understand pathologies, they have their limits.

Accordingly, there are a number of disadvantages of existing systems and methods that can be addressed.

BRIEF SUMMARY

Implementations of the present disclosure solve one or more of the foregoing or other problems in the art. One of the main challenges for implantable biomedical sensing schemes is obtaining a reliable signal while at the same time maintaining biocompatibility. The present disclosure demonstrates that a combination of medical ultrasound detection and smart hydrogel micromechanical resonators can be employed for continuous monitoring of glucose or other biomarker analyte concentrations. The sensing principle described herein is based on the shift of the mechanical resonance frequencies of smart hydrogel structures induced by their volume-phase transition in response to changing analyte levels. This shift is evident, and can be measured as a contrast change (e.g., change in mean grayscale value) in the ultrasound image data due to a change in the degree to which the resonance frequency ultrasound waves is absorbed, when the smart hydrogel biosensor is probed or queried by ultrasound at or near the resonance frequency.

This concept eliminates the need for implanting complex electronics or employing transcutaneous connections for sensing biomedical analytes in vivo. In addition, it is important to emphasize that such methods do not actually require generation of a typical ultrasound image, as all that is required is to track the change in ultrasound response, due to the change in resonance frequency of the smart hydrogel. The present disclosure includes proof-of-principle testing demonstrating that monitoring of ionic strength and glucose concentration using such methods is possible.

Smart hydrogels are attractive in such a use due to their good biocompatibility and versatility. They can be tailored to selectively sense a variety of different analytes by employing different techniques such as molecular imprinting, incorporation of aptamers or inclusion of functional groups inside the polymer network that would be capable of reversible binding to a desired biomarker analyte. Such smart hydrogels may be formed from a hydrophilic network of polymers that experiences a change in volume and/or a change in other mechanical or other physical properties in response to specific stimuli, including contact with a desired analyte, such as glucose, or another biomarker.

While a variety of methods have been proposed for detecting such changes in a smart hydrogel, for example, measurement of swelling of a confined smart hydrogel in a perforated pressure sensor, detection of the bending of a hydrogel coated cantilever structure, changes in electrical properties, optical properties, weight, or elastic modulus, most of these proposed sensing schemes would require a transcutaneous tethered connection (wire or optical fiber) or the implantation of active electronic components to be able to detect that a change has occurred. Such limits their use to critical and short-term continuous monitoring scenarios.

Medical ultrasound can provide a platform for non-harmful remote sensing and therefore eliminate the need for transcutaneous connections or implanted electronics. Troïani et al. "Ultrasonic Quantification Using Smart Hydrogel Sensors", *Talanta* 2011, 83, 1371-1375 reported on an ultrasound-based approach for the quantification of analytes with smart hydrogel particles in liquid environments where the quantification was based on changes in multiple points of the frequency spectrum of smart hydrogel particles in an analyte liquid that occurred as the hydrogel particles underwent a volume change in response to environmental stimuli. However, hydrogel particles are not well suited for implantation since they could travel inside the body, and it would be desirable to have an in vivo sensor that remains generally in place, where implanted. It would be further advantageous if such a sensor would not require subsequent removal.

In addition, the quantification of the analyte in the studies of Troïani was based on calibration and training data, complicating the proposed method. Park et al., "A Wireless Chemical Sensing Scheme Using Ultrasonic Imaging of Silica-Particle-Embedded Hydrogels (Silicagel)". *Sensors Actuators, B Chem.* 2018, 259, 552-559 reported on a sensing method based on ultrasound imaging of a block of smart hydrogel containing embedded silica particles as a contrast-enhancing agent, where the volume change of the smart hydrogel alters the density or dispersion of the contrast agent particles inside the hydrogel, thereby resulting in a shift in the mean grayscale pixel intensity of a selected window in the ultrasound image. However, the use of contrast-enhancing agents inside the hydrogel (such as silica beads or particles) poses a biocompatibility risk, as it is possible for these particles to leach out of the polymer network over time. In addition, such a method requires generation of an ultrasound image, and that the hydrogel block with embedded silica be sufficiently large to visualize the changes. For example, ultrasound may typically only provide resolution of about 0.5 mm, requiring changes to be on this scale, in order to visualize them in an ultrasound image. Advantageously, the present systems do not necessarily require generation of an ultrasound image, or geometric measurements taken from such an image, and can be employed in hydrogel structures that are smaller than 0.5 mm in thickness.

The present disclosure provides a novel approach for sensing of biomedical or other analytes based on resonance absorption of ultrasound in smart hydrogel resonator structures that eliminates the need for contrast agents, and does not require any electrical or other signal connection exterior to the patient. This approach simply uses smart hydrogel-based structures (e.g., sheets, pillars, and/or other structures demonstrating resonance) as the sensing component, and the hydrogel swelling response is queried remotely using ultrasound waves, where the frequency of the ultrasound query is at or near a resonance frequency of the hydrogel sheet, pillar or other resonance structure. While this can be used to detect analyte presence and/or concentration in the body as described herein, it can also be used in other environments, where detection of a target analyte is desired (e.g., in a petroleum or other product pipeline). The geometry of such smart hydrogel-based structures is not limited to sheets or pillars, but extends to a wide variety of geometries, which exhibit the needed resonance absorption characteristics. Non-limiting examples of such shapes include sheets, pillars (cylindrical with a circular cross-section, or pillars having other cross-sectional shapes such as rectangular, square, oval, star-shaped, other polygons, etc.), domes, pyramids, triangular prisms, cubes, other rectangular prisms, etc.).

The Examples herein demonstrate the viability of this approach by presenting in vitro measurements of ionic strength and glucose changes using commercially available medical ultrasound equipment to make the query. The advantages of combining both ultrasound and smart hydrogels demonstrate the potential of this sensing platform technology for continuous in vivo monitoring of biomedical analytes and other sensing applications. Advantageously, this sensing principle is independent of the type of smart hydrogel used so long as it exhibits a volume-phase transition upon changed environmental analyte concentration, and the geometry of the smart hydrogel is selected to exhibit a resonance frequency at the ultrasound frequency used to query the smart hydrogel. The present approach is highly versatile as smart hydrogels can be made sensitive to a wide range of biochemical analytes, other than glucose, and can be fabricated to exhibit the needed resonance characteristics.

In particular, a system according to the present disclosure can be configured for identifying one or more changes in a smart hydrogel microresonator structure positioned within an in vivo or other environment and having a resonance frequency in an ultrasound range. Such a system can include a smart hydrogel microresonator structure (e.g., including at least one of a microresonator sheet or a microresonator pillar), where the smart hydrogel microresonator structure is positioned within the in vivo or other environment and is configured to exhibit a change in resonance frequency in response to interaction with one or more predefined analyte biomarkers in the in vivo or other environment. The system further includes an ultrasound transducer for querying the smart hydrogel microresonator structure within the in vivo or other environment, at or near the resonance frequency of the smart hydrogel microresonator structure. A computer system can also be provided, in electrical communication with the ultrasound transducer, the computer system having one or more processors, where the computer system is configured to receive ultrasound data (e.g., image data) from the ultrasound transducer, such data being provided by query of the smart hydrogel microresonator structure by the ultrasound transducer at or near the resonance frequency. The computer system is also configured to determine (e.g., at the one or more processors) the change in resonance frequency, a change in mean grayscale value (MGV), or a change in amplitude or intensity of the ultrasound wave or pulse associated with the ultrasound data of the smart hydrogel microresonator structure due to a change in the resonance frequency of the smart hydrogel microresonator structure as induced by interaction of the one or more predefined analyte biomarkers with the smart hydrogel microresonator structure in the in vivo or other environment.

In an embodiment, the computer system receives, from the ultrasound transducer, ultrasound data of the smart hydrogel microresonator structure at a first time and at a second time, and the computer system determines a change in resonance frequency or the change in MGV or the change in ultrasound wave or pulse amplitude or intensity of the smart hydrogel microresonator structure based on differences in the ultrasound data (e.g., image or other data) of the smart hydrogel microresonator structure at the first time and as compared to at the second time. It is not necessary that any ultrasound image data provide sufficient resolution to quantify a length or other geometric change in the hydrogel, as the change in geometry is not required to be measured. Rather, its effect on resonance frequency or a parameter affected thereby (e.g., MGV or reflected wave amplitude), is measured.

It is important to recognize that MGV (which is related to an ultrasound image) is not the only parameter that could be measured, to detect the change in resonance frequency. For example, the intensity or amplitude of the measured ultrasound wave (emitted and/or reflected) can be measured, without any need to actually reference MGV or other intermediate. In principle the whole measurement principle can be summarized as follows: 1) an ultrasound pulse of known frequency and amplitude is emitted by the transducer; 2) the pulse transverses the medium (e.g., body tissue, where losses occur (e.g., due to scattering, dampening, etc.), reducing the ultrasound wave amplitude; 3) the pulse reaches the hydrogel structure, where in the hydrogel, the amplitude of the wave or pulse is changed (e.g., attenuated) according to the swelling state of the hydrogel (which correlates to the analyte concentration); and 4) after the pulse has traversed the hydrogel structure and is reflected back, the real-time status of the hydrogel is imprinted in this extra loss in amplitude. Once this pulse (in part or whole) reaches the detector (either in transmission or by reflection of the whole or part of the pulse) this information can be extracted by measuring the pulse amplitude or intensity with the timing of the pulse being used to determine if the pulse interacted with the hydrogel structure or not. Such effect can be further enhanced if the reflected pulse interacts with the hydrogel structure twice. The reflected wave amplitude after interaction with the hydrogel is thus the key parameter that can be evaluated, either directly, or indirectly through another related parameter (such as MGV). Choice of query or probing frequency is important, and can strongly influence the resulting time-domain signal. Careful selection of query or probing frequency enhances the signal-to-noise ratio in the observed change in ultrasound wave amplitude or intensity, making selection of such query or probing frequency very important in an in vivo or similar complex, uncontrolled environment.

In an embodiment, the smart hydrogel microresonator structure advantageously does not include any markers, contrast agents, or external connections, but is a simple hydrogel structure. For example, the structure may consist or consist essentially of the hydrogel, without any smart "chip" electrical components. Various structures that do not interfere with the biocompatibility and simplicity of the smart sensor, such as a polymer substrate, a scaffold or the like as described herein may optionally be present.

In an embodiment, the smart hydrogel microresonator structure is in the form of a sheet. In another embodiment, the smart hydrogel microresonator structure is in the form of a substrate (e.g., a backplane) with one or more pillars extending therefrom. Free pillars without fixation to a backplane, as well as numerous other possible structural geometries are also possible. Elimination of any backplane in a given structure may reduce response time for a given smart hydrogel microresonator structure to respond to the presence of a given analyte.

In an embodiment, the smart hydrogel microresonator structure has a thickness from 100 μm to 1000 μm, or from 150 μm to 500 μm, and may have a length from 0.1 mm to 20 mm, or 1 mm to 20 mm, or from 2 mm to 20 mm.

An embodiment may include a control hydrogel also positioned within the in vivo or other environment, where the control hydrogel is configured to not change resonance frequency in response to interaction with the one or more predefined analyte biomarkers.

In an embodiment, any change in dimension or volume of the smart hydrogel microresonator as a result of interaction with the one or more predefined analyte biomarkers in the in vivo or other environment may not necessarily be readily detectable in the ultrasound image itself, as the scale of such change may be too small to be perceptible in such an image, given the limited resolution of ultrasound imaging. As described herein, generation of an ultrasound image is not actually required.

Associated methods of use are also disclosed, allowing a practitioner to monitor concentration of a given analyte, using the smart hydrogel microresonator structure implanted in the in vivo or other environment, as queried by the ultrasound transducer at or near the resonance frequency of the microresonator structure.

Another embodiment is directed to an implementation where the smart hydrogel microresonator structure is provided on or in a tip of an intravenous catheter, positioning the microresonator structure into the intravenous environment during use. Such a microresonator structure could be configured to be sensitive to a drug or any other substance, e.g., as delivered through the IV (e.g., an anesthetic such as fentanyl). Ultrasound query as described herein allows a practitioner to monitor the concentration of such drug or other desired target analyte in near real time, at the catheter location.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

In the drawings, multiple instances of an element may each include separate letters appended to the element number. For example, two instances of a particular element "100" may be labeled as "100a" and "100b." In that case, the element label may be used without an appended letter (e.g., "100") to generally refer to every instance of the element, while the element label will include an appended letter (e.g., "100a") to refer to a specific instance of the element. Similarly, a drawing number may include separate letters appended thereto. For example, FIG. 1 may include FIG. 1A and FIG. 1B. In that case, the drawing number may be used without the appended letter (e.g., FIG. 1) to generally refer to every instance of the drawing, while the drawing label will include an appended letter (e.g., FIG. 1A) to refer to a specific instance of the drawing. The disclosure will be described and explained with additional specificity and detail through the use of the accompanying drawings in which.

DETAILED DESCRIPTION

Figure 1A:
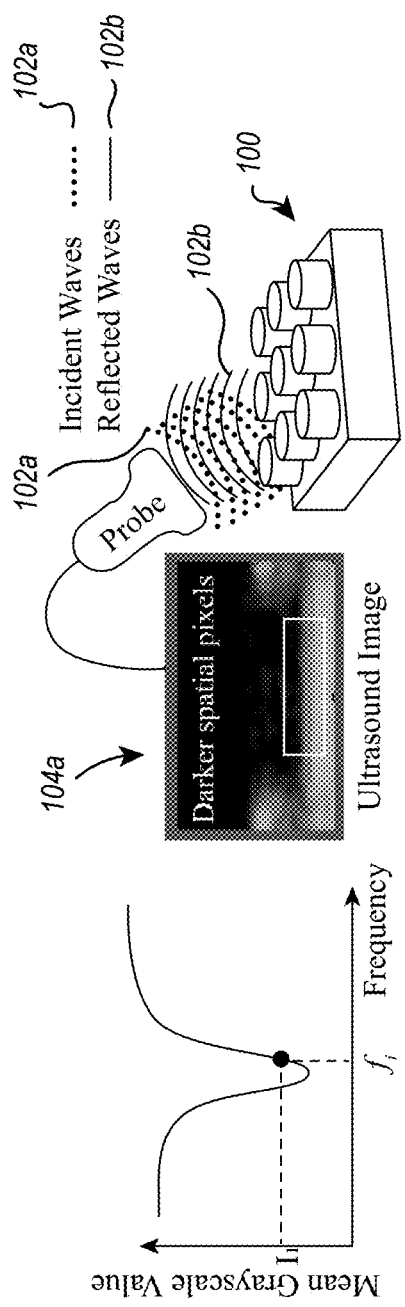
FIGS. 1A-1B schematically illustrate the present ultrasound read-out mechanism for a smart hydrogel resonator structure, where ultrasound waves are generated by the probe, and the reflections are recorded by the receiver elements, e.g., on the same probe. The intensity and timing of the returning waves in each spatial location are used to determine the pixel grayscale value of a corresponding point in a generated ultrasound image. A mean grayscale value may be determined for an area including a plurality of such pixel points in the image.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments, and is not necessarily intended to limit the scope of the claimed invention.

Ultrasound and Hydrogel Sensing

As discussed above, medical imaging devices are generally limited in the kind information that can be reported. Ultrasound, for example, generally relies on sonically reflective surfaces to produce an image and provides little information outside of image data. Normally, ultrasound lacks the resolving power to identify the presence or absence—let alone the concentration—of biomarkers within the body. The combined use of ultrasound and smart hydrogel microresonator structures, however, can be adapted for this purpose. As described herein the presently contemplated solutions can be a standalone sensing solution with a corresponding ultrasound transducer that does not require the generation of an image or even calculations associated with image generation. Rather, as described herein, the present methods can be achieved more directly, based on ultrasound pulse/wave detection (particularly changes in intensity or amplitude) alone.

Hydrogels are structures that include hydrophilic cross-linked networks of polymer that have both liquid-like and solid-like properties. Smart hydrogels characteristically experience a change in their volume and mechanical properties in response to the presence of a specific stimulus or analyte, particularly where the hydrogel incorporates functional groups that can reversibly bind to the target analyte. For example, aptamers (e.g., short single strands of nucleic acids such as DNA or RNA) can be incorporated into the hydrogel, allowing it to selectively bind to target biomarkers (e.g., glucose, proteins, other peptides, opioids, other drugs or drug metabolites to be detected, etc.) to allow the smart hydrogel to serve as a identifier of whether and how much of the target analyte is present.

As used herein, the term "analyte" is to be construed broadly, and includes any substance that can itself be identified or measured or of which a chemical or physical property thereof can be identified or measured. Analytes include, for example, nucleic acids, proteins, other peptides, or other compounds. Glucose is a specific example of an analyte. In some instances, analytes serve as a physiologic, pathologic, or environmental markers of a known or unknown phenomenon (e.g., glucose or insulin levels can serve as a biomarker for diabetes). It should be appreciated that the disclosed embodiments apply generally to smart hydrogels that are responsive to any desired target analyte.

Hydrogels can also respond to the presence of an environmental stimulus (e.g., temperature, pH, gas, osmolarity, humidity, etc.) and can additionally serve to indicate particular state data of an aqueous solution, such as pH. That is, hydrogels can change their volume and/or mechanical properties in response to the level of salinity or acidity in an aqueous solution. The present systems and methods can be used to detect and measure such.

A hydrogel can transition from a collapsed or shrunken state to a swollen state in response to the presence (or absence) of a specific analyte. Such a change is typically not binary, but the degree of change is gradual, depending on the concentration of analyte present in the environment of interest. Of course, the concentration of the analyte can span any particular concentration along a spectrum of concentration values, from relatively low, to relatively high. Thus, in other words, the change in volume of the hydrogel due to the presence of the target analyte can correlate to the concentration of the analyte, and the system can be calibrated to provide such analyte concentration data to a user of the system, based on the changes to the hydrogel detected.

The hydrogel is configured to swell or otherwise change volume (e.g., shrink) in response to interaction with the target analyte in response to the concentration of analyte present. The biomarker sensitive hydrogel can be configured to reach an equilibrium within a given time period based on the concentration of analyte available.

To now, the ability to obtain a real-time, visual readout of hydrogel responses to analytes or other stimuli has proven problematic, particularly when the hydrogel is implanted in vivo or in another demanding environment. Noninvasive medical imaging techniques would be an ideal method to obtain a real-time, visual readout of hydrogel responses in vivo, but hydrogels are normally nearly invisible to most medical imaging devices—including ultrasound—making it difficult to determine any response of the hydrogel to surrounding analytes and/or stimuli. Thus, even though hydrogels represent a promising material for biomedical and biotechnological applications, their lack of visibility and concomitant lack of ability to be tracked in real time using current imaging devices and techniques has made their potential unrealized.

The present disclosure provides a novel approach for sensing of biomedical analytes based on resonance absorption of ultrasound in smart hydrogel resonator structures, without the need for any contrast agents. This approach uses smart hydrogel-based structures (e.g., sheets, pillars or any of a wide variety of other geometries that exhibit resonance absorption) as the sensing component, and the hydrogel swelling or shrinking response is queried remotely using ultrasound waves, where the ultrasound waves are specifically selected to be at or near a resonance frequency of the hydrogel structure.

Sensor Concept

In B-mode (also known as 2D mode) ultrasound imaging, a linear array of transducers sends and receives ultrasound waves to and from a medium to create a 2D image based upon the timing and intensity of the incident and reflected waves. While such 2D mode ultrasound imaging can be used as described herein to make the query, it will be appreciated that other modes (e.g., pulse echo mode or others) of ultrasound devices may also be suitable for use. In 2D mode imaging, the reconstructed 2D image represents a 2-dimensional cross-section of the medium, and the intensity of each pixel in the image is the logarithmic ratio between the intensities of the incident and reflected waves from the corresponding spatial point. The change of acoustic impedance when transmitted between two media types determines the amount of the ultrasound signal that is reflected from the boundary. Boundaries with closely matched acoustic impedances do not exhibit considerable contrast in the ultrasound image. As the acoustic impedances of hydrogel and the surrounding aqueous medium are very similar due to the high water content of the hydrogel, the intensity of the reflections from the hydrogel/solution boundary is very small. Therefore, using ultrasound imaging directly to assess the swelling state of hydrogel provides only limited information.

To solve this challenge, the present disclosure uses smart hydrogel geometries that are specifically patterned into micromechanical resonator structures. In the simplest case such a resonator can be just a sheet of hydrogel having a thickness of about a hundred to a few hundred microns. More complex arrays of pillar-like resonator structures could potentially offer a faster response time due to the reduced distance the analyte needs to diffuse into the hydrogel. However, this may come at the cost of a reduced signal strength as the effective ultrasound absorption area of such a pillar structure is reduced compared to a sheet.

Ultrasound waves are mechanical compression waves, and as such can excite mechanical vibrations in structures they pass through. When the proposed smart hydrogel resonator structures are probed by ultrasound waves having a frequency close to one of their mechanical resonance frequencies, they start to vibrate with a higher amplitude by absorbing mechanical energy from the ultrasound waves. This lowers the reflected ultrasound wave intensity and thus creates additional contrast in the ultrasound image, even where there may be a close acoustic impedance match with the surrounding environment.

Any change to the volume or mechanical properties (e.g., elastic modulus) of the smart hydrogel resonators alters their resonance frequencies and, therefore, the amount of energy from the ultrasound waves that is absorbed. The amount of absorption depends on the frequency separation between the resonance frequency and the excitation frequency (i.e., the ultrasound waves used for making the query), such that the closer the query frequency is to the peak resonance frequency, the more pronounced the effect will be. This resonance induced absorption changes the ultrasound wave intensity being reflected back to the ultrasound transducer, and thus changes the observed pixel gray scale value in the resulting ultrasound image. This concept of using resonance frequency for the query enables the measurement of small changes in the smart hydrogel induced by changing analyte concentrations, even where the hydrogel structures themselves are so small that the volumetric change due to swelling or shrinking may not be ascertainable in the image data. Indeed, no image at all even need be generated or displayed for the present methods and systems to work.

Figure 1B:
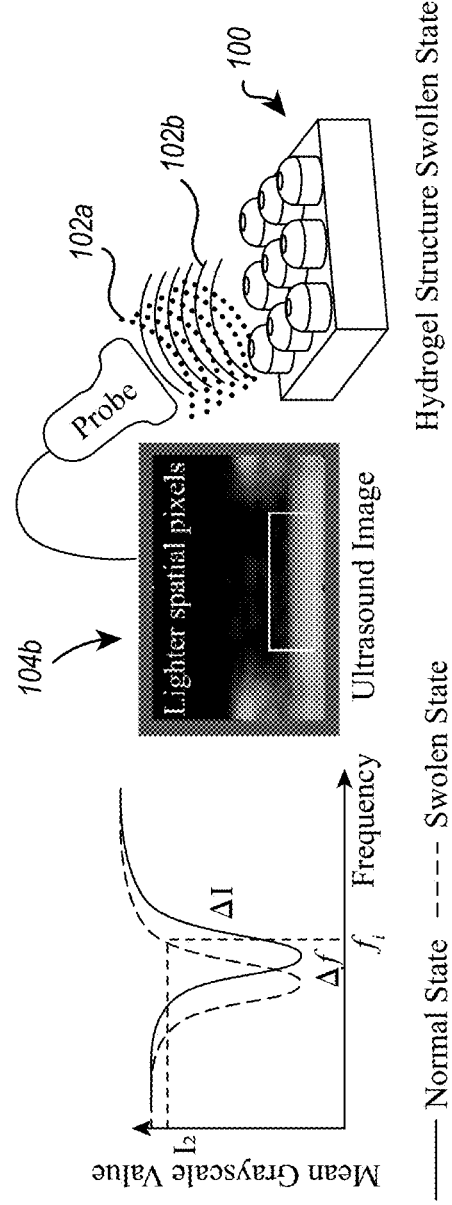

FIGS. 1A-1B schematically illustrate the proposed sensing concept. For example, a micromechanical resonator structure 100 (e.g., a resonator sheet or an array of hydrogel pillars on a hydrogel backplane) is imaged using medical ultrasound (incident waves 102a and reflected waves 102b) at a frequency close to one of the mechanical resonance frequencies of the micromechanical resonator structure 100. In the normal state (FIG. 1A), the structure 100 (e.g., an array as shown) has a specific mean grayscale value (MGV) in the ultrasound image 104a (MGV1). If, for example, the hydrogel structure 100 swells, the resonance frequency shifts and as a result the MGV of the pixels in the ultrasound image 104b changes (MGV2). The changes in the spatial MGV of the pixels (ΔMGV) can, therefore, be correlated to changes in the swelling state of the hydrogel structure 100. It is worth noting that the relevant spatial dimensions of the ultrasound resonator structures 100 (which are typically permitted to expand in 3 dimensions), are on the order of the wavelength of the ultrasound waves (e.g., about 100 to a few hundred microns), such that their changes cannot be readily observed in the image.

Figure 1C:
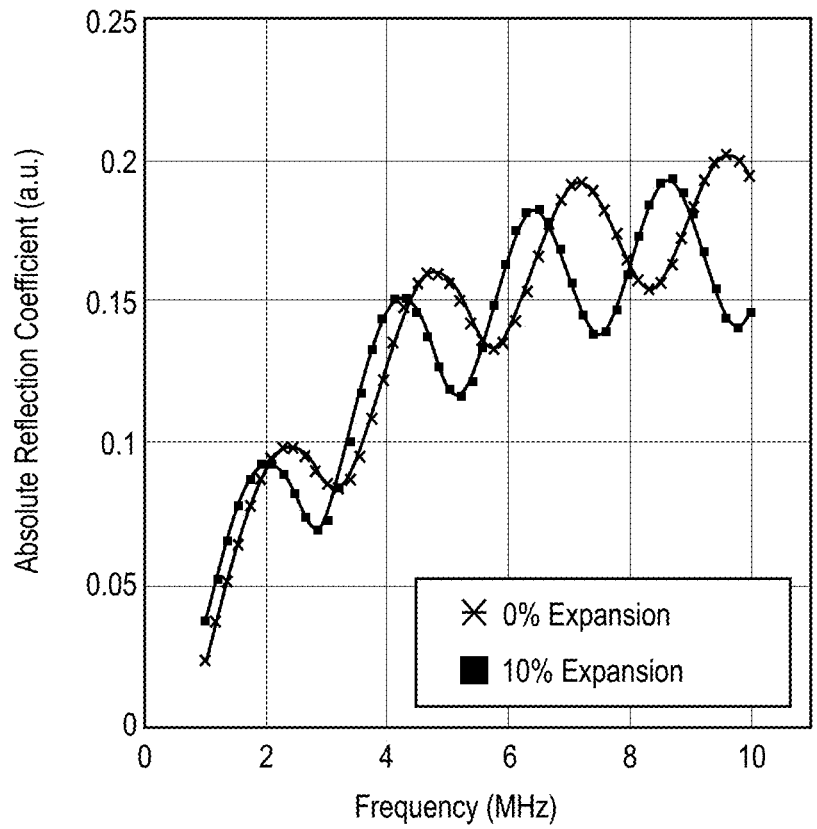
FIG. 1C shows reflection coefficient versus frequency for an exemplary smart hydrogel resonator structure, in an expanded, and un-expanded state, based on a simulation.

By way of example, FIG. 1C illustrates absolute reflection coefficient (arbitrary units) versus frequency for a hydrogel microresonator sheet having a thickness of 279 μm, on a polyimide film with a thickness of 25 μm, where the calculations are based on a simulation and finite element analysis of such structure. As shown in FIG. 1C, there is a significant and easily detectable shift in the reflection coefficient between the un-expanded hydrogel resonator sheet, and the same sheet, once it has undergone 10% expansion. By way of example, 4.8571 MHz corresponds to a resonance peak of such a resonator sheet. FIG. 1C shows reflection behavior of the resonator sheet from 1 to 10 MHz. Such reflection is plotted as reflection coefficient, defined as the ratio of average reflected wave pressure to average incident wave pressure. As noted herein, when the hydrogel structure experiences a volume change, the resonance frequency shifts, which will manifest itself as a change in the mean grayscale value associated with the ultrasound image in the region of the hydrogel. The concentration of the analyte (e.g., glucose or any other analyte) can be correlated to this shift.

In general, any mechanical resonance mode of the hydrogel structure that can be excited by ultrasound can be employed for the present methods. Possible mechanical resonance modes of a given hydrogel structure depend on the geometry of a hydrogel resonance structure. Cantilever-like structures such as pillars, for example, can easily exhibit one or more of longitudinal, flexural or torsional resonance modes. If the frequency of the ultrasound waves is close to (e.g., within 30%, within 25%, within 20%, within 10%, or within 5% of) a resonance frequency of the structure, the corresponding resonance mode can be excited.

Perhaps the simplest to understand resonance mode for both pillars and sheets (and combinations thereof) are longitudinal resonance modes, although other resonance modes could also be excited using the principles described herein. Such longitudinal resonance modes can be described as longitudinal standing compression waves between the top and bottom surface along the thickness of the sheet or along the pillar axis. The resonance frequency of such modes can be analytically approximated, for example, as a thin rod of a solid material in air. However, the boundary conditions in the case of a smart hydrogel structure in liquid may be less well defined. In addition, in case of arrays of pillars, the individual resonators may interact with each other via the substrate they are attached to, which may further complicate the estimation of the frequency response of the array. Due to such complexity, numerical methods such as finite element simulations may be employed to guide resonance frequency estimations and resonator design, as noted above relative to FIG. 1C.

In any case, the resonance frequency of these modes depends on the material properties of the resonator material (e.g., speed of ultrasound waves therethrough) and the distance between the top and bottom surface. In the exemplary case of an expansion of a smart hydrogel structure, the elastic modulus typically decreases, the volume and thus the internal distance between surfaces increases and the density decreases due to the increase in water content of the hydrogel. How strong these individual effects are depends on the hydrogel composition. It is possible that some effects could cancel each other out, at least to some degree (e.g., the influence of changes in elastic modulus and density may oppose one another). As a result, the change in the distance between surfaces (e.g., the thickness of the hydrogel sheet or pillar), effectively an increase of the resonator length will likely dominate and result in an overall downward shift in resonance frequency.

The shift in resonance frequency can be detected directly in the frequency domain (e.g., tracking a change in resonance frequency), can be detected by observing the changes in the MGV in the ultrasound image data (corresponding to a change in intensity of the reflected ultrasound waves) at a specific frequency, or can be detected by simply measuring the wave or pulse intensity at a given frequency (e.g., as may be done in preparation to generate an ultrasound image, although but the present methods do not require image generation). Such is illustrated in FIGS. 1A-1B. As the resonance frequency shifts downwards, the intensity changes with a sign and magnitude that depend on the location of the imaging/excitation frequency on the frequency spectrum relative to the position of the resonance peak (i.e., how close the ultrasound frequency being used for the query is to the resonance frequency of the hydrogel structure).

Figure 1D:
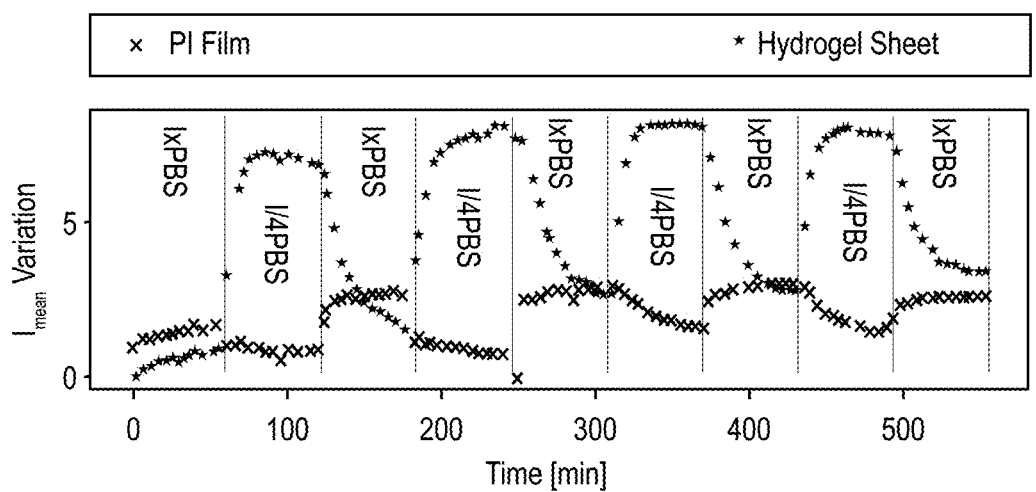
FIG. 1D shows variation in intensity ($I_{mean}$) of mean grayscale value on an 8 bit scale for an exemplary smart hydrogel resonator structure in different concentrations of PBS, based on experimental data.

FIG. 1D shows change in average pixel intensity (i.e., MGV) of the same exemplary hydrogel resonator sheet as in FIG. 1C, where the sheet has a thickness of 279 μm on a 25μ polyimide film, where the sheet is imaged using a conventional ultrasound imaging system at 4 MHz. FIG. 1D also tracks the variation in MGV for a polymide film without any hydrogel sheet thereon. The minimum has been offset to 0 for the sake of simplicity. One main advantage of such sensors is the complete separation of the readout unit from the implanted device. The remote nature of the sensor and system significantly enhances its ability to meet desired biocompatibility or other environmental constraint characteristics, and reduces complexity of the sensor and overall system. In addition, ultrasound is already readily available in many clinical settings, and is a very safe diagnostic tool, which would enable fast adoption of such systems in clinical environments.

In some embodiments, the hydrogel microresonator structure (e.g., such as a sheet or pillar) can be relatively small, e.g., less than 0.5 mm thick so as to be capable of injection into a desired location through a narrow gauge needle, or similar implantation technique. In an embodiment, the hydrogel resonator structure may be elongate in shape, or at least include an elongate structure therein (e.g., a sheet or pillar), such that the width or diameter of such structural portion is disproportionate to its length. Such shapes may be well suited to exhibiting resonance frequencies within the desired range. In an embodiment, a given portion of the hydrogel resonator structure can have a thickness greater than 5 μm, greater than 10 μm, greater than 20 μm, greater than 30 μm, greater than 40 μm, greater than 50 μm, greater than 70 μm, greater than 80 μm, greater than 90 μm, greater than 100 μm, greater than 150 μm, greater than 200 μm, less than 1000 μm, less than 500 μm, less than 400 μm, or less than 300 μm. For example, a given resonator sheet may have a thickness from 100 μm to 500 μm, or from 100 μm to 300 μm. Any included pillars may also have micro size dimensions, e.g., less than 150 μm, less than 100 μm, less than 90 μm, less than 80 μm, less than 70 μm, less than 50 μm, less than 40 μm, less than 30 μm, less than 20 μm, or less than 10 μm in height, diameter, or spacing between adjacent pillars. By way of example, exemplary pillars (e.g., positioned on a substrate, providing an array of such pillars) may have a height of from 10 μm to 50 μm or from 15 μm to 40 μm, may have a diameter from 20 μm to 100 μm, or from 40 μm to 80 μm, and a spacing between pillars of 1 μm to 50 μm, or from 5 μm to 20 μm. Such values are of course merely provided as examples. An exemplary hydrogel array in the form of a disc including a substrate backlayer and a plurality of pillars may be such that the backlayer is sized according to the sheet values provided above (e.g., 100 μm to 300 μm thick), and the pillars are sized according to the pillar values provided above. One such structure described in the Examples (and shown in FIG. 2D) had a thickness of less than 0.5 mm, and an overall diameter of 8 mm. In general the thickness of a resonator sheet, pillar, or other resonator structure may be adapted to the ultrasound frequency used for query and may typically be from about 25% to about 100% of the ultrasound wavelength in the hydrogel or other applicable medium, where it is intended to excite the longitudinal resonance of such structure.

Figure 6A:
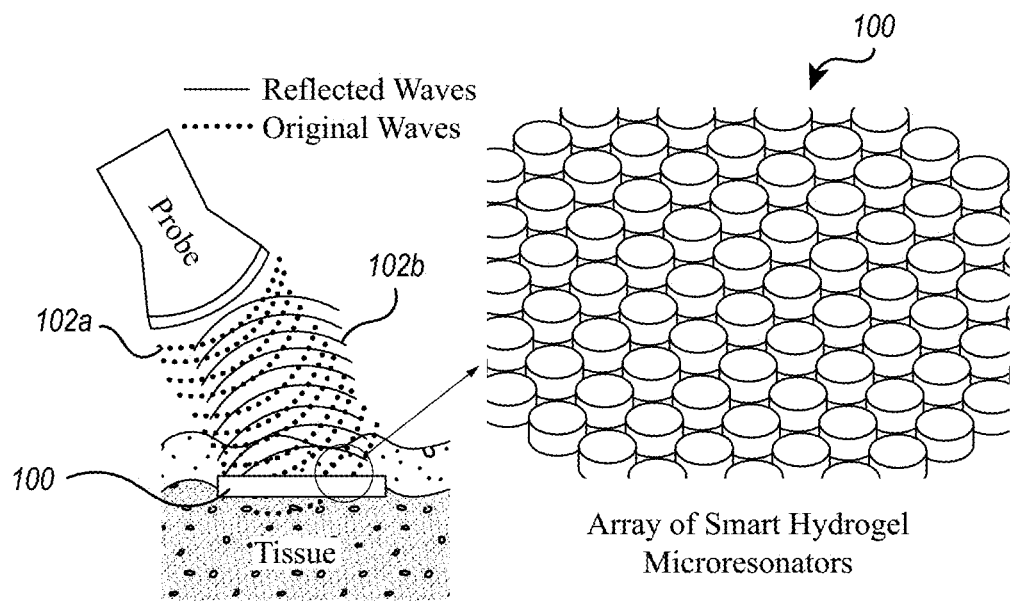
FIG. 6A schematically illustrates a method and system for in vivo querying of a smart hydrogel microresonator structure.
Figure 6B:
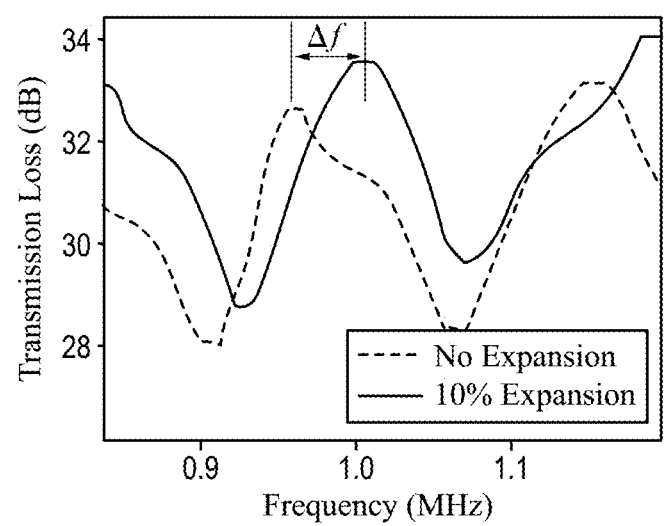
FIG. 6B plots transmission loss versus frequency for conditions in which the smart hydrogel microresonator structure is expanded versus non-expanded, based on a simulation.

FIG. 6A schematically illustrates a system and method according to the present disclosure, similar to that shown in FIGS. 1A-1B, showing use in an in vivo environment, where the hydrogel microresonator structure 100 is implanted subcutaneously, and is queried with incident ultrasound waves 102a, resulting in reflected waves 102b. FIG. 6B illustrates transmission loss versus frequency, showing how the peak transmission loss (i.e., associated with resonance absorption) shifts (by Δf) the resonance frequency. Such a shift in resonance frequency, or the resulting change in mean grayscale value (MGV) can be tracked, and correlated to the concentration of a given analyte in the in vivo or other environment being monitored.

MultiPlexing/Exclusion of Readout

A challenge when using such techniques may be multiplexing—the reading out of multiple analytes that may be present within the same environment. Such a multiplexing issue can be addressed by using differently scaled microresonator structures that have their target resonance frequency in different regions of the frequency domain of which the ultrasound transducer is capable of. For example, it will be apparent that different resonator sizes result in different resonance frequencies, where relatively smaller resonators exhibit relatively higher resonance frequencies. It is important to ensure that resonance peaks of given differently scaled microresonator structures do not overlap (minimizing or eliminating overlap of the target resonance frequency peak as well as higher order harmonics). Each of these structures can be fabricated from a smart hydrogel specifically configured to detect a different target analyte. Such microresonator structures can be implanted together in the same in vivo or other environment resulting in a mixture of differently scaled microresonator structures. In doing so, the individual absorption maxima of the incident and reflected ultrasound waves can be attributed to different microresonator structures, which each have their independent sensitivities to different target analytes. By probing the area at different resonance frequencies that are exhibited by the various microstructures, a multi-analyte assay or multiplexing can be realized.

Figure 7A:
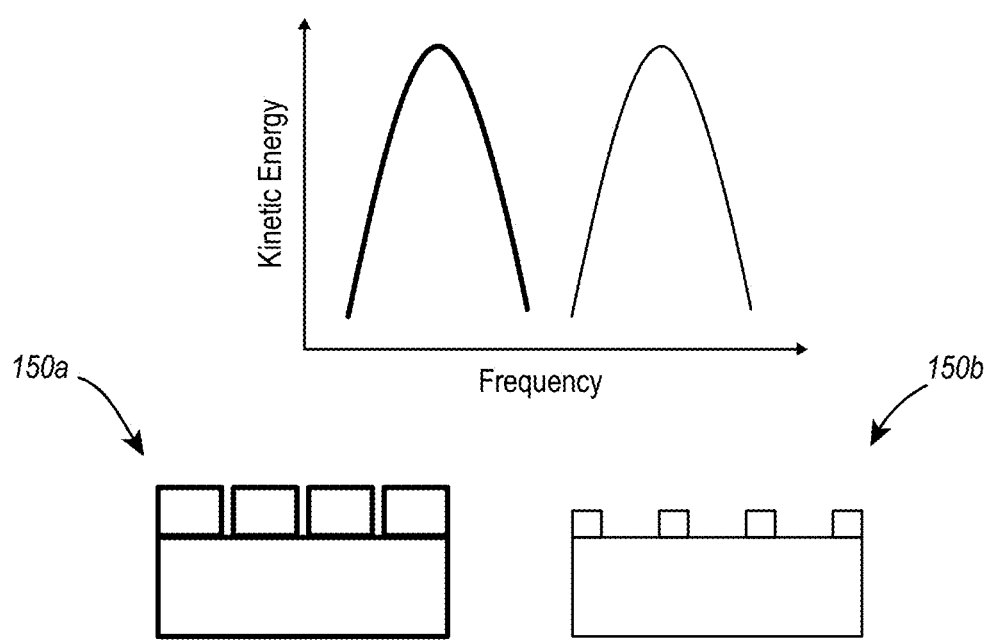
FIGS. 7A-7C illustrate concepts for multiplexing multiple analytes by employing microresonator structures having different spatial dimensions (and different peak resonance frequencies).
Figure 7B:
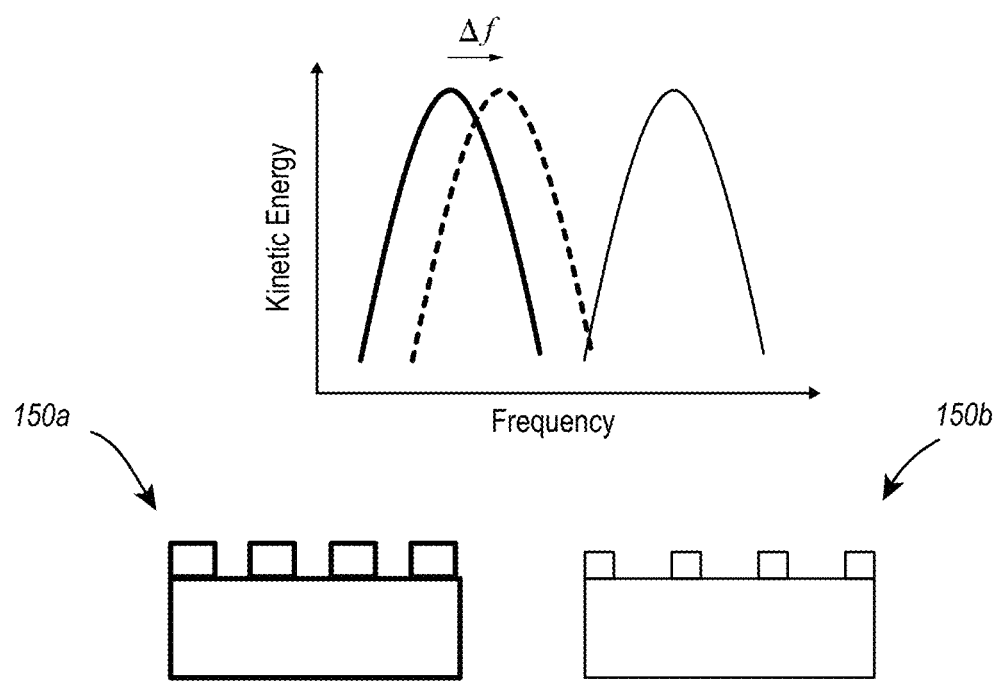
Figure 7C:
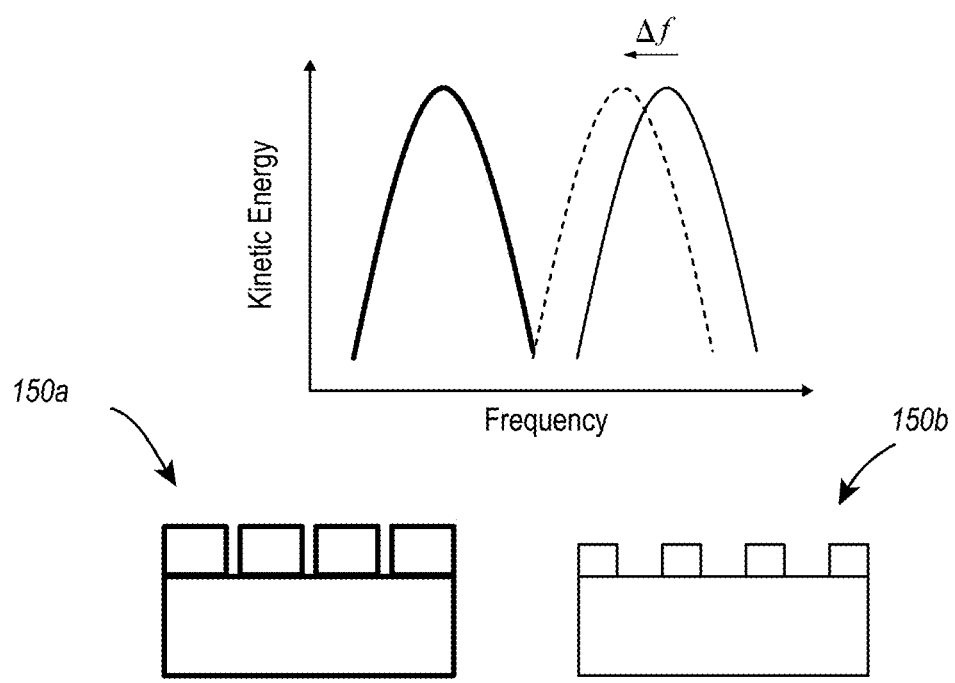

FIGS. 7A-7C illustrate such an embodiment. For example, FIG. 7A schematically illustrates two differently scaled microresonator structures 150a and 150b, each of which include different resonance frequency peaks which do not overlap, as illustrated. As shown in FIG. 7B, upon exposure to a first analyte to which microresonator structure 150a is sensitive, first microresonator structure 150a changes (e.g., shrinks), causing a Δf shift in resonance frequency. As shown in FIG. 7C, upon exposure to a second analyte to which microresonator structure 150b is sensitive, second microresonator structure 150b changes (e.g., swells), causing a Δf shift in resonance frequency. As shown in these Figures, when in contact with just the first analyte, the second microresonator structure 150b that is configured to be sensitive to the second analyte, does not react in any substantial way, but the resonance frequency of the second microresonator remains substantially unchanged. Similarly, when in contact with just the second analyte, the first microresonator structure 150a that is configured to be sensitive to the first analyte, does not react in any substantial way, but the resonance frequency of the first microresonator remains substantially unchanged.

Free Floating Smart Hydrogel Microresonators Confined in a Scaffold

Many embodiments as described herein provide a microresonator sensing structure that is configured as a resonator sheet, or an array of hydrogel pillar microresonators extending from a backplane. Such a backplane may be made from the same hydrogel material as the pillars, or another substrate material such as a sheet of a biocompatible polymer (e.g., polyimide). This configuration with a backplane is helpful to keep the pillar sensor structures connected, and to prevent their dispersion in vivo or through another given environment, which may result in the loss of the ability to track the microresonator structures.

Figure 8:
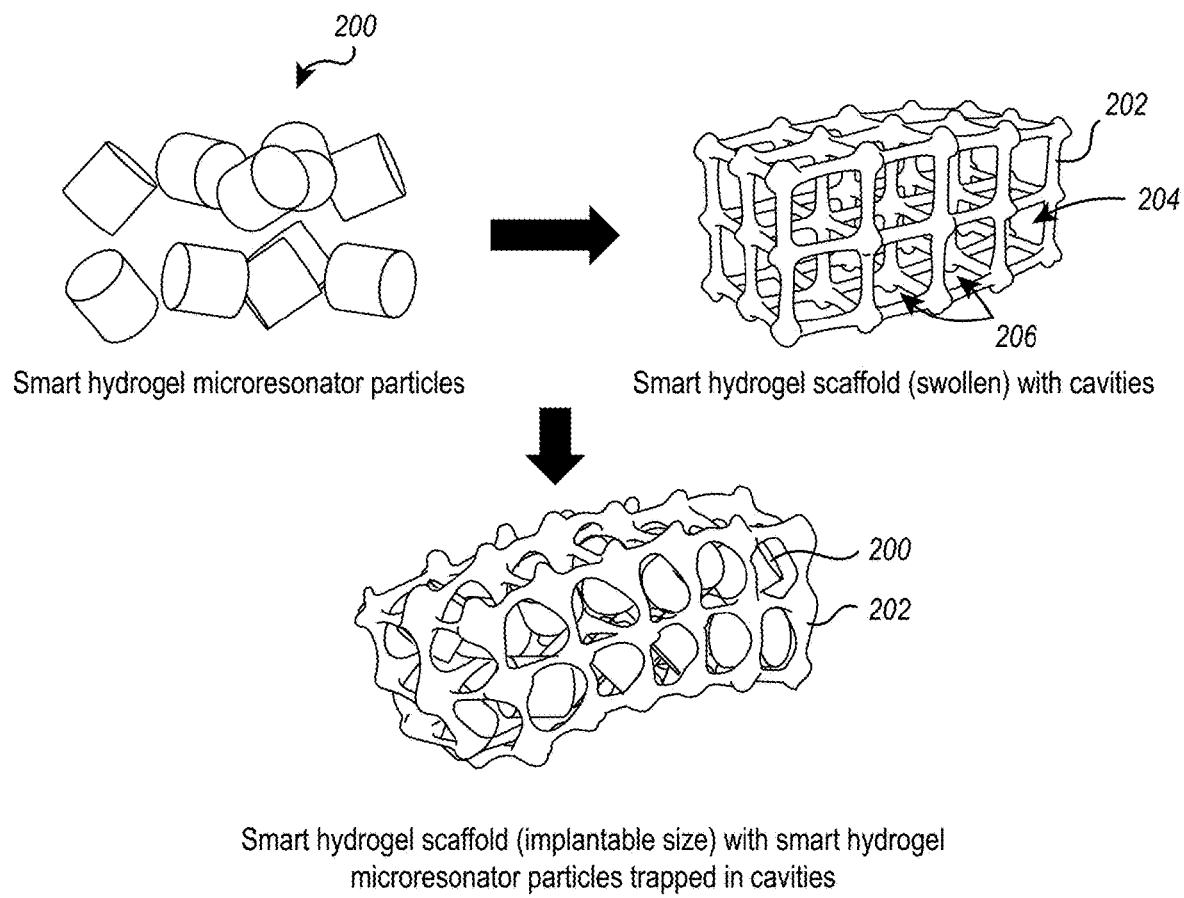
FIG. 8 illustrates entrapment of microresonator hydrogel structures within a scaffold.

An alternative way to achieve a similar ultrasound readout sensing approach as illustrated in FIG. 8 is to use free-floating smart hydrogel microresonator structures 200 (e.g., pillars, or other elongate geometry having a desired resonance frequency), but which are confined within a scaffold 202. Such a scaffold 202 that can be made from a porous hydrogel or a polymer. It is not necessary that the scaffold be formed from the smart hydrogel, capable of shrinking or swelling, as any suitable material such as a biocompatible polymer can be used for the scaffold. Such a scaffold 202 includes a cavity 204 large enough to contain one or more of the free-floating microresonator structures 200 (e.g., pillars or particles). Any opening(s) 206 into the cavity 204 when in the in vivo or other detection environment should be small enough to trap the resonators 200 within. During manufacture, the cavity 204 and/or openings 206 can be enlarged by intentionally swelling the scaffold 202 and introducing the microresonator particles 200. After the particles or other microresonator structures 200 are inside the cavity 204, the hydrogel scaffold 202 can be shrunken thus confining the resonator particles 200 inside. For the resonators to still work, the cavity 204 should be larger than the unswelled resonators 200, providing room for expansion. Such porous hydrogel scaffolds can be fabricated for example by direct laser writing photopolymerization or cryogelation. Homogenously sized hydrogel resonator pillar-like particles 200 can be, for example, manufactured by microfluidic channels and chrome-mask-based photopolymerization, and then washed out of the channel. This concept enables a greater variety of geometries for the implantable sensor devices, especially elongated ellipsoidal shapes well suited for implantation through a small gauge needle. Furthermore, if the scaffold 202 is made from hydrogel, but without any resonance frequencies in the ultrasound range used for query, it will advantageously transmit the ultrasound waves with very low attenuation.

Biodegradable Smart Hydrogel Sensor Devices

Figure 9:
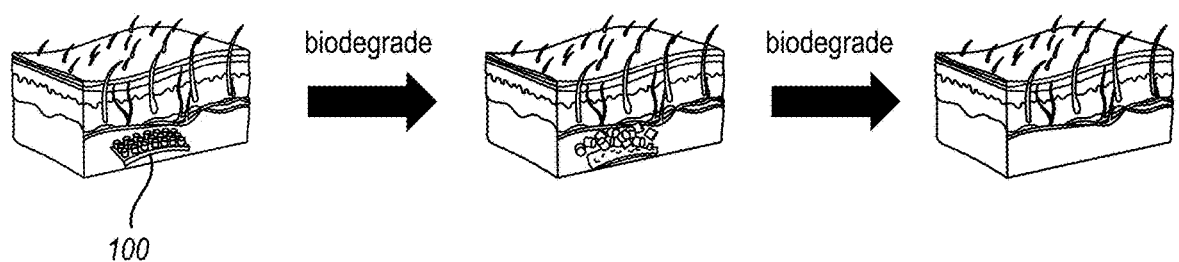
FIG. 9 illustrates progressive biodegradation of a biodegradable smart hydrogel microresonator structure in an in vivo environment, as described herein.

Hydrogels can be designed to biodegrade and have the potential to exhibit a very high biocompatibility due to their large water content and tunable mechanical properties. Biodegradable polymers and biomarker-specific molecules such as aptamers or other chemical moieties used to bind to the target analyte can be used to ensure all components of the hydrogel microresonator structure are biodegradable, so that the sensor device can be implanted in vivo, with no need for removal. Providing a fully biodegradable smart hydrogel microresonator structure configured for ultrasound readout capable of injection into the human body through a small gauge needle (e.g., gauge 16 to 30, 18 to 30, 20 to 30, or 25 to 30) is particularly advantageous, particularly where there is no need for subsequent removal of the microresonator structure. FIG. 9 schematically illustrates how such a biodegradable microresonator structure 100 may be implanted subcutaneously, and can automatically begin to biodegrade after a given period of time (e.g., 7 to 180 days, 1 week to 3 months, 1 week to 1 month, such as about 14 days).

One issue with implantable biomedical sensor devices is that they have to be inserted and eventually removed causing a significant amount of discomfort to the patient. This is the major obstacle for some patients alongside cost and risk of complications. A biodegradable microresonator structure as described could circumvent such issues, where the sensor itself is easily injected similar to an insulin injection and has the ability to naturally break down into harmless components, which are removed by the human body after a given amount of time.

The benefit of a biodegradable microresonator structure stems from the controlled dissolution of the hydrogel in vivo over a specified timeframe. Such a microresonator structure may exhibit the key characteristics outlined in Table 1 below. Of course, In addition, the smart hydrogel microresonator structure needs to be biocompatible, meaning its composition must be designed in such a way that the materials used are non-toxic and can be safely biodegraded naturally and internally by the human body over time. Another important characteristic is the miniaturization of the general resonator structure as well as optimization of any protective packaging thereof to minimize mechanical restrictions to the vibration of the resonator structure by surrounding tissue, etc. Hydrogel resonator structures along with any necessary support structure would ideally be scaled down to sub 500 µm scale to be able to be injected through a small-gauge needle. Where the injected hydrogel microresonator structure may be difficult to locate using ultrasound, it may be possible to provide the structure with a biocompatible and/or biodegradable tracking structure, which can be included for increased visibility/tracking.

Examples of biodegradable hydrogels materials may be those based on compositions that can include one or more of, but not limited to, poly(ethylene glycol), poly(methyl methacrylate), hyaluronic acid, chitosan, alginate, gelatin, heparin, chondroitin sulfate, aliphatic polyesters, oxidized dextran, bovine serum albumin, cellulose, carboxymethylcellulose, propylene glycol, collagen, and/or poly(vinyl alcohol).

As noted, in summary, the hydrogel composition may advantageously biodegrade over a specific time. The hydrogel composition is advantageously configured and selected to allow for easy aptamer or other recognition element integration, thereby, creating a single hydrogel platform that can be modified with aptamers or other recognition elements for selectivity. The present smart hydrogel materials are advantageously able to be molded or structured to elicit an ultrasound response, and the smart hydrogel structures can be injectable to form a localized subcutaneous microresonator structure sensor.

TABLE 1

| Requirement | Description |
| --- | --- |
| Biocompatibility | All the components of the hydrogel need to be in vivo compatible |
| Controlled Expiration | The hydrogel decomposition needs to be controlled |
| Size | Ex vivo fabricated hydrogels need to be small enough for injection |
| Crosslinking initiator | Needs to be biocompatible |
| Non-immunogenic | Cannot elicit an immune response |
| Recognition element | Phenylboronic acid, glucose aptamers, glucose oxidase, glucose-binding protein, etc. |
| Structured | Be able to be molded or structured either in vivo or before injection |

Catheter-Mounted Smart Hydrogel Ultrasound Resonator for IV Analyte Monitoring

Continuous monitoring of drug concentrations in blood plasma can be beneficial to guide individualized drug administration. High interpatient variability in required dosage and a small therapeutic window of certain drugs can cause risks and challenges during administration, for example in case of anesthetic medications. The present embodiment provides a sensing platform concept using a smart hydrogel microresonator sheet with ultrasound readout that is integrated into or onto a catheter (e.g., onto the top of a catheter).

This concept is validated in-vitro using glucose as an easy to access and handle target analyte. In the case of continuous glucose measurement, a working example of the present novel catheter mounted sensing platform allows the detection of glucose concentrations in the range of 0 mM to 12 mM. Such a platform provides the potential to provide continuous monitoring of various intravenously applied medications. Selectivity to different drugs, e.g., fentanyl or any other desired medication or other analyte can be accomplished with an appropriately designed smart hydrogel composition.

Sedative and analgesic drugs are administered perioperatively to facilitate medical procedures, e.g., surgery, and to manage postoperative pain. In clinical anesthesia, determining the right dose is critically important and challenging at the same time, because the window representing drug concentrations that are safe, effective, and efficient is very small. Additionally, the pharmacokinetics and dynamics are highly nonlinear, time variant, and have a large interpatient variability.

Conventional drug monitoring methods such as liquid chromatography-tandem mass spectrometry (LC-MS) and enzyme-linked immunosorbent assays (ELISAs) provide the advantages of high selectivity and sensitivity, however, their dependence on larger lab settings, and being multi-step techniques as well as having slow processing time do not lend themselves for clinical anesthesia. Instead, anesthesiologists currently rely on estimating hypnosis from the processed EEG or using surrogate measures indicating anesthetic drug side effects or autonomic nervous system activity, such as respiration, blood pressure, or heart rate. These measures are combined with information relative to the patients' comorbidities, demographics, and type of surgery, to dose anesthetic drugs.

The continuous monitoring of drug concentrations in blood plasma could be an important tool to help with setting the right dose. Such feedback on drug levels in near real time would decrease the mental workload of experienced anesthesiologists and might in the future allow for automated closed-loop systems for drug administration. A smart hydrogel-based sensor system as described herein can be a promising tool in this regard. Smart hydrogel based intravenous analyte concentration monitoring systems have the possibility of fulfilling most of the continuous drug sensing requirements such as biocompatibility, selectivity, implantability, sensitivity (within an analyte's physiological range), and reversibility.

Figure 10:
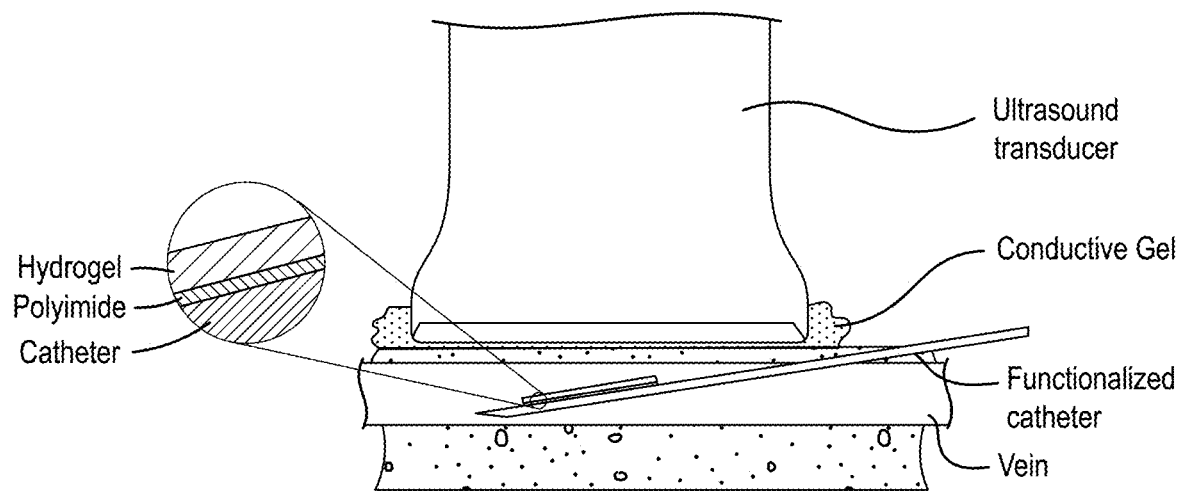
FIG. 10 illustrates an embodiment including a smart hydrogel resonator hydrogel structure integrated onto a tip of a catheter for IV drug monitoring.

As described herein, the employed sensing principle is based on the swelling-state-dependent oscillation response of a smart hydrogel resonator sheet or other microresonator structure. Ultrasound is used to read out the hydrogel's analyte-dependent swelling state. If the hydrogel layer is excited by ultrasonic waves of fixed frequency, the ultrasound response changes depending on the concentration-dependent hydrogel swelling state. Readout is based on a change in the intensity of the reflected ultrasonic waves as a result of an analyte concentration-induced change in the hydrogel's volume, and hence resonance frequency. In the ultrasound image, the intensity change is expressed as changes in mean grayscale value of an area of the ultrasound image that corresponds to the location of the smart hydrogel structure. Evaluation of MGV changes or another parameter as described herein (e.g., tracking of changes in amplitude or intensity of the ultrasound wave or pulse) allows tracking the analyte concentration. In the working example described herein, this resonance absorption of ultrasound waves in catheter tip-mounted smart hydrogel structures can be used for continuous monitoring of analyte concentrations. For example, a smart hydrogel resonator structure (e.g., sheet) is fixed on the tip of a catheter which is then introduced into the intravenous space (FIG. 10). The ultrasound probe can be used to track the smart hydrogel's swelling state. While the working example was conducted with glucose, the system can be adapted to detect the concentration of drugs (e.g., fentanyl) or any other desired analyte.

EXAMPLES

Example: Hydrogel MicroResonator Sheets and Arrays

The following examples demonstrate the viability of the proposed measurement principle in vitro. The examples actually carried out include both microresonator sheets as well as a combined resonator structure including a sheet-like backplane with an array of hydrogel pillars extending therefrom.

Preparation of pre-gel solutions: the polyampholytic smart hydrogels used in the present examples are sensitive to glucose as well as pH and ionic strength. The pre-gel monomer solution was prepared by using DI water to prepare a 1 mM buffer solution of 4-(2-hydroxyethyl)piperazine-1-ethanesulfonic acid (HEPES). To this 1 mM HEPES buffer was added an appropriate amount of acrylamide needed to obtain a 30% w/w monomer solution. Next 19.1 mg of the anionic monomer 3-acrylamidophenylboronic acid was dissolved in 257 µL of the 30% w/w solution of acrylamide in 1 mM HEPES buffer and mixed with 87 µL of dimethyl sulfoxide and 20.48 µL of the cationic monomer N-[3-(dimethylamino)propyl]methacrylamide. In addition, to this pre-gel solution was added 193 µL of a 2% w/w solution in DI water of the crosslinker N,N'-methylenebis (acrylamide), and 25.8 µL of a solution in 1 mM HEPES containing 4% w/w of the photoinitiator lithium phenyl-2, 4,6-trimethylbenzoylphosphinate. Finally, 309 µL of 1 mM HEPES buffer was added to bring the volume of the pre-gel solution up to 900 µL.

Preparation of test solutions: phosphate-buffered saline (PBS) solutions used in all experiments were prepared, containing 10 mM sodium phosphate, 1.8 mM potassium phosphate, 137 mM NaCl, and 2.7 mM KCl) This formulation corresponds to a 1×PBS solution. Lower concentrations of PBS were prepared by diluting the 1×PBS with DI water correspondingly.

A solution of 6 mM glucose was made by dissolving 18.106 g of dextrose in 180 mL of 1×PBS solution and then increasing the volume by adding 1×PBS to obtain 200 mL of a 500 mM glucose solution. In order to obtain 50 mL of a 6 mM glucose solution in 1×PBS, 0.6 mL of 500 mM glucose was added to 49.4 mL of 1×PBS.

Figure 2A:
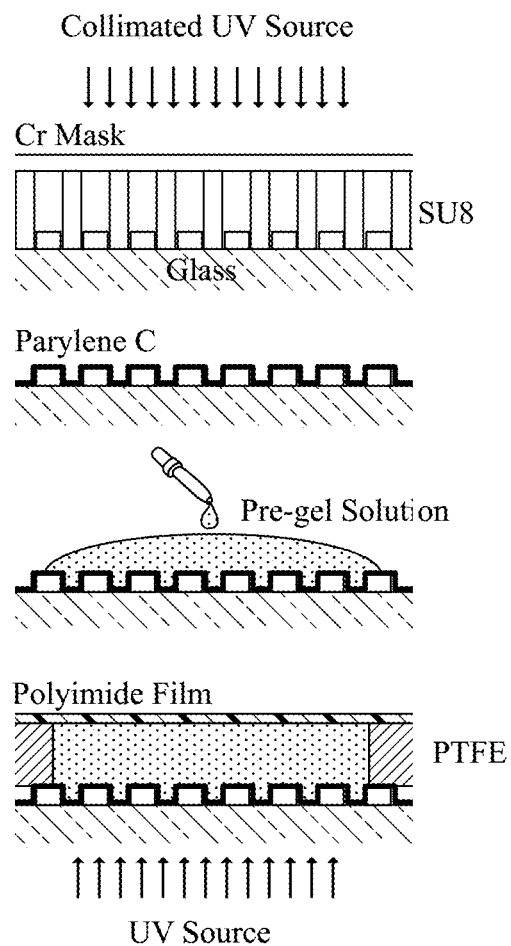
FIG. 2A schematically illustrates an exemplary molding process that can be used to form a hydrogel structure.
Figure 2B:
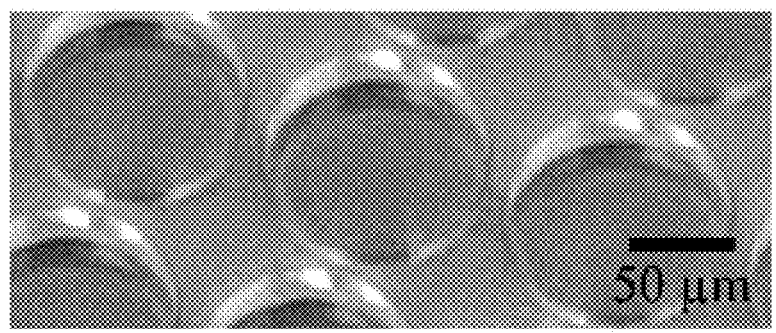
FIG. 2B is an optical microscope image of fabricated pillar array molds.

Fabrication of hydrogel samples: smart hydrogel sheets of given thicknesses can be fabricated by simply using corresponding polytetrafluoroethylene (PTFE) spacer molds. Replica molding techniques can be used for more complex structures. Standard techniques using PDMS molds tend to fail for chemically cross-linked hydrogels synthesized by free-radical crosslinking copolymerization due to adhesion of the hydrogel to the mold and inhibition of the process by the free-radical scavenging behavior of oxygen. This becomes even more severe as the feature size scales down to a few tens of microns due to the faster diffusion of oxygen into smaller features. In order to overcome this challenge, molds were fabricated using photolithography on a 30 µm thick SU8 photoresist (SU8-2025) on a 700 µm thick borosilicate glass substrate. The fabricated structures were then treated with Parylene adhesion promoter (Silane A-174) in the gas phase. They were then coated with a ~3 µm layer of Parylene-C to avoid adhesion of the hydrogel during the molding process. FIG. 2A shows an overview of the molding process for the hydrogel pillars.

To fill the molds the pre-gel solution was purged with argon gas for 10 min to reduce its oxygen content and was then dispensed on the surface of the mold away from its center and placed under a low vacuum to prevent or lessen the impact of gas being trapped in the mold structure. Next, the pre-gel solution was dispersed over the whole surface by tilting the mold. In the case of smart hydrogel sheets the pre-gel solution was subjected to the same treatment. The only difference was that instead of a mold, a simple Parylene-C covered glass sheet was used as a substrate.

Figure 2C:
FIG. 2C is an optical microscope image of hydrogel pillars, as formed.

After removing the samples from the vacuum, a PTFE spacer of the desired backplane thickness was placed on the mold surrounding the dispensed solution. A 25 µm thick polyimide (PI) film was then placed over the spacer and pre-gel solution. The PI film was surface modified to promote adhesion to the hydrogel. This film attaches to the hydrogel during polymerization of the pre-gel solution and later helps to peel off the hydrogel resonators from the mold. Additionally, it provides support for the hydrogel structures for future handling. The pre-gel solution was polymerized by exposing it to UV light at a wavelength of 365 nm for three minutes through the glass substrate. Subsequently, the hydrogel structures were carefully removed from the mold with the help of the attached PI film. FIG. 2C shows the formed pillar array structures after removal from the mold. The hydrogel structures were then conditioned by washing cycles in PBS, with the ionic strength switched between 1×PBS and ¼×PBS five times. These variations of PBS concentration induce an alternate swelling and deswelling of the hydrogel which gradually results in the removal of un-crosslinked molecules trapped inside the polymer network. This step is helpful to ensure a consistent swelling response from the hydrogel. Finally, all structures were checked for uniformity using optical microscopy.

Figure 2D:
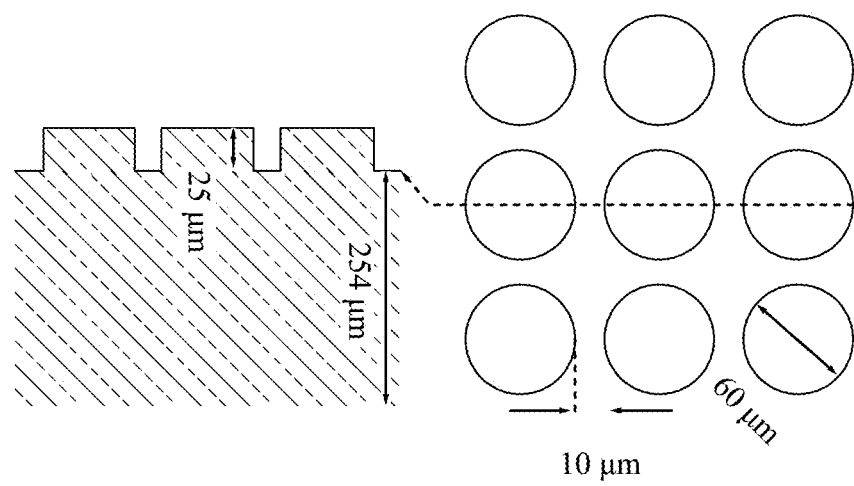
FIG. 2D shows cross-sectional views of an exemplary fabricated hydrogel microresonator structure, including a backplane, and a plurality of pillars extending therefrom.

Experimental ultrasound measurements: using fabrication methods described herein, more complex hydrogel resonator structures including a backplane of smart hydrogel and an array of pillars protruding from its top surface as shown in FIG. 2D (and 6A), was formed.

The fabricated samples were cut into discs measuring 8 mm in diameter using a biopsy punching tool and each sample was mounted with the PI on a 3D printed polylactic acid (PLA) sample holder with an inner diameter of 9 mm and an outer diameter of 11 mm with the PI carrier film at the bottom. The sample holder facilitates handling and also makes it easier to locate the hydrogel structure in the ultrasound image. The completed samples were then mounted in the bottom of a container together with control samples containing only a PI film in the sample holder. The samples were always kept submerged in 1×PBS solution to keep them hydrated throughout the experiment.

A medical ultrasound imaging system (ACUSON S2000, Siemens Medical Solutions USA, Inc.) was used to image the devices in different concentrations of PBS and glucose solutions using an ultrasound probe with frequencies ranging from 4 to 9 MHz (9L4, Siemens Medical Solutions USA, Inc.). The probe was fixed on top of the devices vertically at a focal distance of 3 cm (minimum possible focus length for the probe) and the imaging axis was adjusted to the center of all the samples to maximize the area of the hydrogel being imaged. The container was fixed on the stand to avoid any possible movement of the samples relative to the ultrasound probe.

In the imaging systems control software, the power was adjusted to 100%, and the dynamic range was set to its maximum possible value (90 dB) in order to maximize the sensitivity of the pixel intensities to variations in the intensity of the reflected ultrasound waves. All the imaging enhancement parameters were turned off to access images with minimum manipulation from the instrument, and the image tint was set to 8-bit grayscale. In all experiments, solution exchanges were done manually using a silicone tube attached to a syringe. For any solution exchange, the samples were rinsed three times with the target solution to ensure complete removal of the old solution around the samples before introducing the target solution.

Data analysis: In evaluative post processing the images taken from the system were stabilized for possible translational offsets of the devices relative to the ultrasound probe throughout the experiments using an algorithm which is suitable for the stabilization of medical images that was provided as an add-on to the Image J software package. The selection of a specific region across all images over time was examined visually to ensure the effectiveness of the algorithm.

A box of 100×20 pixels was chosen at the interface of the PLA and solution, which contains the polyimide and hydrogel. The position of the box was kept constant throughout all images. The mean grayscale values, MGV, of these 100×20 pixel selections were calculated using the following equation, where $n_i$ is the number of the pixels in the box with a gray scale value of i between 0 to 255.

$$MGV = \frac{n_1 + 2n_2 + 3n_3 + \ldots + in_i + \ldots + 255n_{255}}{\text{Total number of pixels} = 2000}$$

The location of the box around the hydrogel sheet was chosen manually at the beginning of the evaluation and the size of the box was chosen arbitrarily but was kept constant in all experiments for consistency.

The initial gray scale value of the evaluated area was found to be somewhat arbitrary, depending on the initial environment and position of the sample with respect to the ultrasound probe. As this makes it difficult to compare the data of different samples, a gray scale value offset was calculated. For this the lowest MGV of the whole data set for a given sample was used as a baseline and subtracted from all data points belonging to the corresponding sample.

Figure 3:
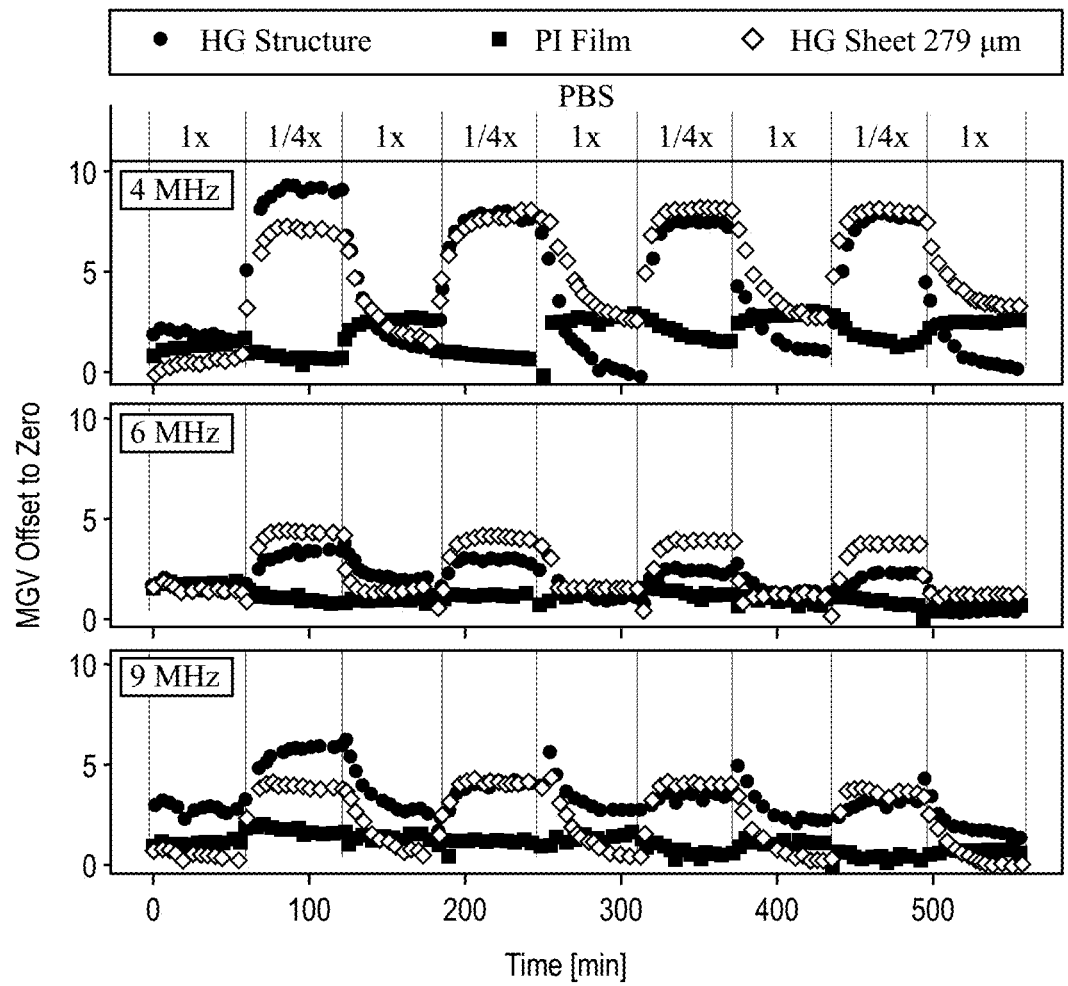
FIG. 3 shows the response of an exemplary microresonator hyrdogel sheet, a microresonator hydrogel structure including pillars on a backplane, and a polyimide (PI) control sample for transitions between two different concentrations of PBS as recorded at 4 MHz, 6 MHz and 9 MHz.

For a comparison between the microresonator in the form of a sheet and the microresonator in the form of a backplane with pillars extending therefrom, the following samples were fabricated: The hydrogel resonator sheet had a thickness of 279 µm. The more complex microresonator, including the backplane and pillars was defined by pillars of 25 µm in height, 60 µm in diameter, with 10 µm spacing between pillars. The backplane was 254 µm thick (see FIG. 2D). An empty PI film was added as a control sample. These samples were then exposed to two different concentrations of PBS (1× and ¼×). The PBS concentrations were cycled four times with one hour measurement time for each concentration. The ultrasound images were collected every 5 minutes at the standard B-mode (2D) imaging frequencies on the probe, namely 4, 6 and 9 MHz. FIG. 3 shows the evaluated data (MGV with offset) for the response of the smart hydrogel sheet, the smart hydrogel resonator structure with pillars and a backplane, and the PI film control sample, each at the three B-mode imaging frequencies.

Figure 4A:
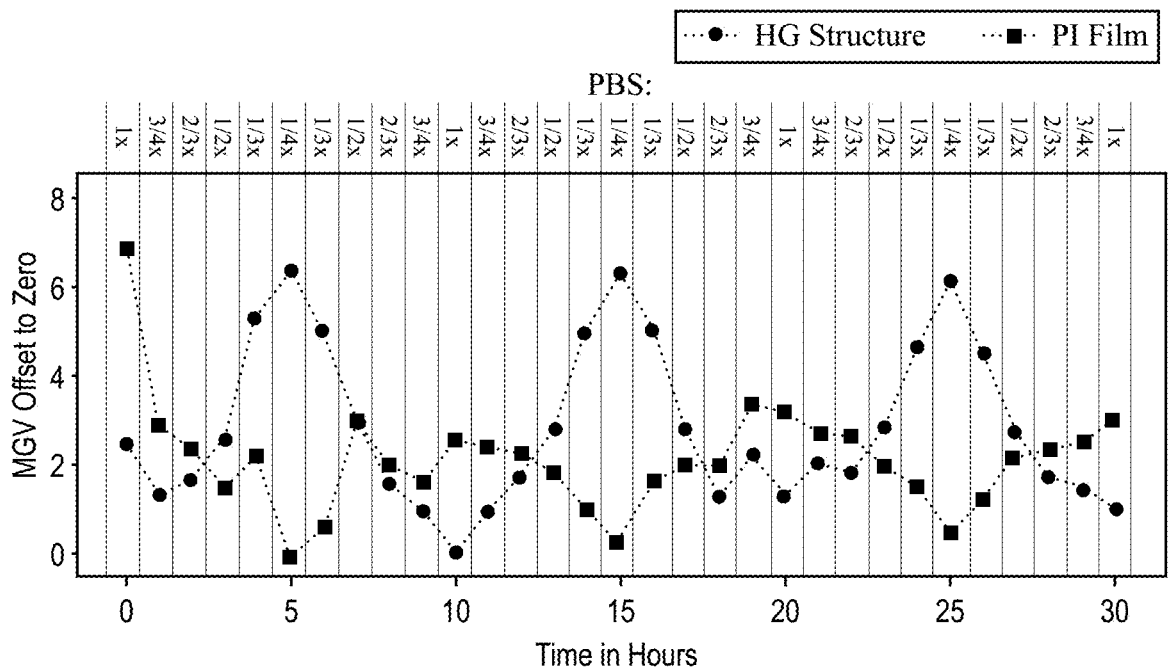
FIG. 4A shows the MGV response of a hydrogel pillar-backplane structure and a polyimide (PI) control to buffered saline across concentration steps between 1×PBS and ¼× PBS.
Figure 4B:
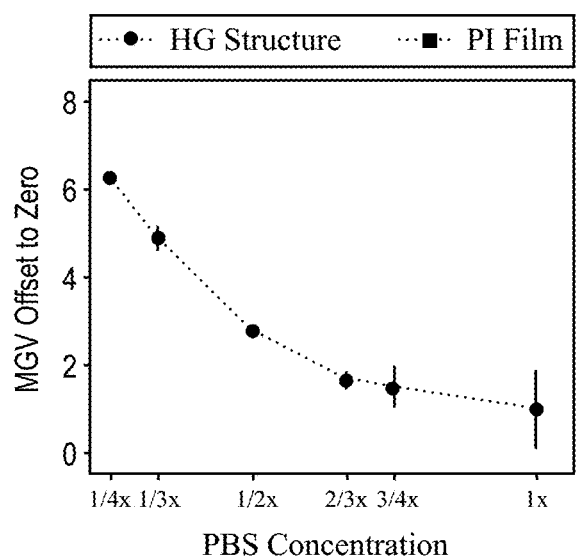
FIG. 4B shows the MGV response of a smart hydrogel pillar-backplane structure to changes in PBS concentration.

In order to better assess the response of the hydrogel pillar-backplane resonator structure to changes in the ionic strength of the environment another batch of the sensing structures according to FIG. 2D was fabricated. This sample along with a PI film control was then subjected to several different PBS concentrations and their repeatability were studied by switching the concentration of the PBS solution between 1×, ¾×, ⅔×, ½×, ⅓× and ¼× for three cycles, as shown in FIGS. 4A-4B. The samples were allowed to stay in the solution for an hour to equilibrate before imaging at 4 MHz for each step. FIG. 4B shows the response of the sensor to different PBS concentrations averaged over the available data points, and the error bars are the standard deviation of the corresponding values.

Figure 5A:
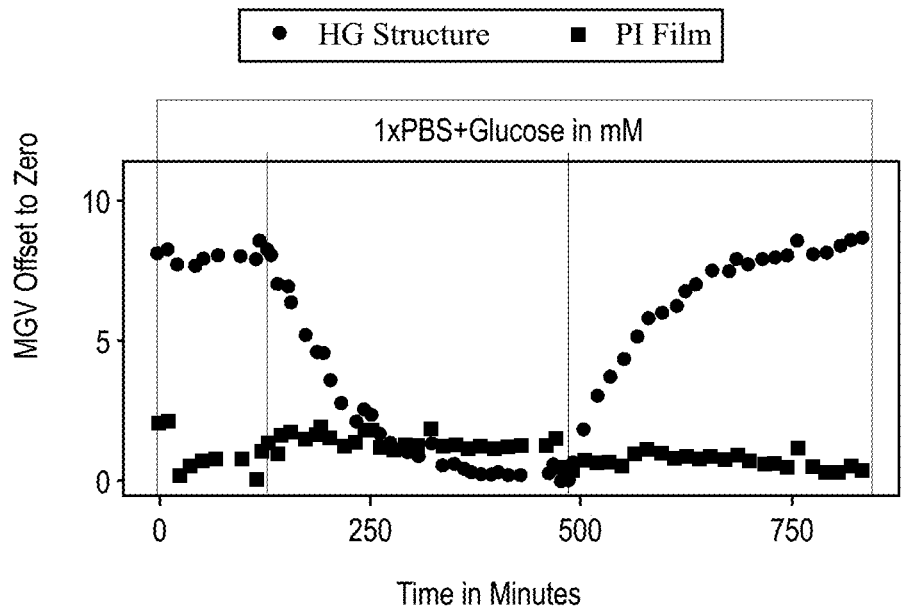
FIG. 5A shows MGV sensor response as a function of time for a solution of 6 mM glucose in 1×PBS.
Figure 5B:
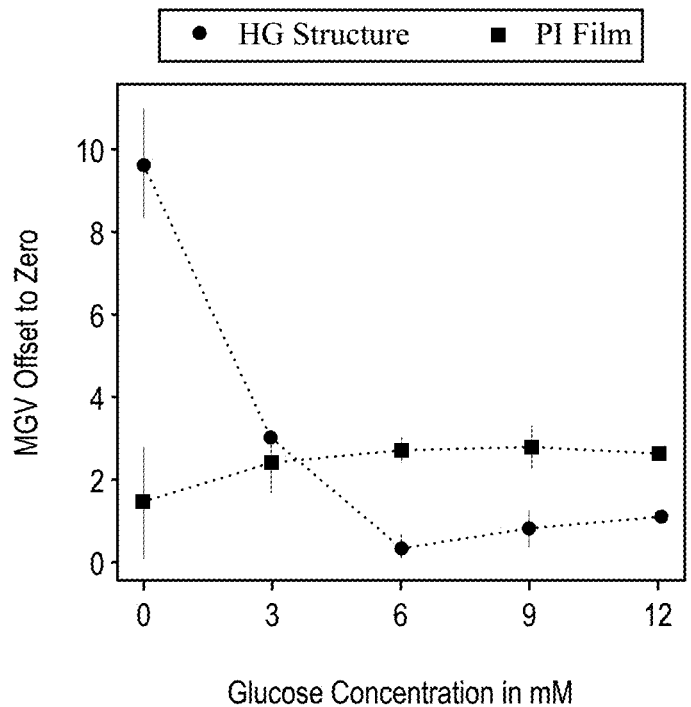
FIG. 5B shows the change in the average pixel intensity (MGV) of the smart hydrogel pillars to changes in glucose concentration in 1×PBS.

The response of the same pillar-backplane resonator structure to relevant levels of glucose was measured as an example of an important biomedical metabolic analyte that could be monitored using this approach. Two experiments were carried out for this. In the first experiment, the response of the structure to the introduction of glucose was studied over time. The structure was allowed to equilibrate overnight in 1×PBS. Then it was first imaged for two hours in 1×PBS and then was exposed to 6 mM of glucose in 1×PBS followed by repeated imaging over 6 hours. Finally, the glucose was removed from the environment, and imaging continued for another 6 hours. Ultrasound images were collected with maximum intervals of 15 minutes. FIG. 5A shows the response of the pillar-backplane structure and PI film control samples at 4 MHz ultrasound query frequency. In the second experiment, the resonator structure was allowed to equilibrate in 1×PBS for 6 hours, and then the concentration of glucose was increased by 3 mM steps up to 12 mM. The concentration of glucose was then returned from 12 mM glucose to no glucose in 3 mM steps. In each step, the microresonators were allowed to equilibrate for 6 hours and then were imaged at 4 MHz. FIG. 5B shows the response of the hydrogel pillar-backplane structure to those glucose levels. The responses resulted from averaging the values obtained for each concentration and the error bars show the standard deviation of those values.

The smart hydrogels used in the examples described herein are configured to shrink as a result of an increase in ionic strength or glucose concentration. Thus, the ultrasound signal gathered from the smart hydrogel resonator samples will react to the presence of these analytes, when probed at or near a resonance frequency of the smart hydrogel microresonator. In terms of the reaction to changes in ionic strength it can be seen in FIG. 3 that at a probe or query frequency of 4 MHz there is a strong signal in response to changes in the PBS concentration and thus ionic strength of the test solution. When immersed in 1×PBS both hydrogel microresonator samples (the sheet and the pillar-backplane structure) show a strongly increased MGV when compared with their state when immersed in ¼×PBS. At 6 MHz and 9 MHz the signal of the hydrogel structures is still present however less pronounced compared to the 4 MHz measurement. The signal magnitude of the steps in the 6 MHz measurement are smaller than in the 9 MHz results. With respect to the proposed sensing principle this could be explained by the presence of longitudinal modes as discussed above as standing waves occur at regular frequency intervals. It is thus likely that the 4 MHz frequency is close to a resonance mode of the hydrogel structures in the test environment. The 6 MHz frequency is likely in between resonance modes and the 9 MHz frequency is likely close to a subsequent resonance mode (e.g., 2nd harmonic). In any case, the data shows proof-of-principle for the contemplated methods and systems. The ultrasound signal in response to changing ionic strength was consistently far above the PI film control.

It was observed that the swelling response of the pillars measured via ultrasound was approximately twice as fast as the shrinking response. In addition, a signal offset appeared to occur for the pillar-backplane hydrogel structure when the solution is exchanged. This is especially evident in the 9 MHz data set, which may be due to trapping of an air bubble in the sample holder. As long as the bubble is stable, such an offset could be subtracted in a sensing application. For the 4 MHz data the control PI film also seems to show a small response to the analyte changes, either as an offset or a small equilibrating signal. The reason for this is unknown but could be caused by changes in the mechanical properties of the test solutions.

To further study the response of the sensing structure to ionic strength another production batch of the pillar-backplane structures was exposed to several different concentrations of PBS in three cycles as shown in FIG. 4A. This data was then evaluated into the sensitivity data shown in FIG. 4B. The response of the sensor in the third 1×PBS step is not consistent with the other PBS steps. A possible explanation for this behavior could be the trapping of air bubbles during the solution exchange. In FIG. 4B the large standard deviation at 1×PBS and ¾×PBS concentrations are due to the abnormal reading in the third cycle. This plot also exhibits a nonlinear sensor response at higher PBS concentrations, which can either be attributed to a saturation in volume change response of the hydrogel or to the position of the imaging frequency compared to the resonance peak. FIG. 1 illustrates an example of a positioning of the imaging frequency relative to the resonance peak which could result in relatively linear intensity response versus concentration.

The time-domain glucose response data, shown in FIG. 5A, shows the response of the sensing structure to a biomedically relevant analyte. Note that the smart hydrogels studied here are configured to shrink with an increase in glucose concentration. The swelling of the hydrogel pillar array that occurs with a decrease in glucose concentration causes an increase in the reflected ultrasound intensity, and deswelling causes a reduction in intensity. This is consistent with the ionic strength response as discussed before. In contrast, the PI film control does not exhibit a meaningful response to changes in glucose concentration. The plot of intensity versus glucose concentration in FIG. 5B shows a good response to glucose up to about 6 mM and then levels off.

In order to transition these successful in vitro experiments to an in vivo stage several differences should be considered. For example, when the sensors are implanted into tissue, the interface between the tissue and the hydrogel might have a lower acoustic impedance mismatch than with the liquid, resulting in a smaller energy transfer to the resonance mode and thus a lower signal. Furthermore, the tissue could mechanically constrain the hydrogel's volume change, thus lowering the signal further. Use of a sonolucent casing or scaffold that allows for unconstrained swelling or shrinking of the hydrogel could address such issues.

To summarize, applicant observed a reproducible and consistent response from the smart hydrogel microresonators for two different analytes, namely PBS (ionic strength) and glucose. Furthermore, the ionic strength data indicates that both the hydrogel microresonator sheets and the pillar-backplane structure show comparable results. The results provide a proof-of-principle of the functionality of the proposed smart hydrogel sensing structures.

The present disclosure presents a detailed discussion of a new sensing approach based upon the resonant absorption of ultrasound in smart hydrogel microresonators, and describes a molding-based method for fabricating microresonator sheets and pillar-backplane structures. Such methods are compatible with mass-fabrication. The disclosure also shows proof-of-concept examples demonstrating measurement of the response of the resonators to changes in ionic strength and glucose concentration.

One of the main advantages of this sensing method is that it can be employed for implantable and continuous biomedical sensing without the need for electronics or transcutaneous wire connections (i.e., contact-free signal transduction). In addition, smart hydrogels can be tailored to respond to a variety of biomedical analytes. Hence, this sensing method is a platform technology that could enable a promising class of implantable sensors with potential for long-term operations in vivo or in other environments. Furthermore, the general availability of ultrasound imaging equipment in clinical environments and the cost-effective and simple fabrication process could support the widespread application of this sensing approach.

Example: Catheter-Mounted Smart Hydrogel

A pre-gel monomer solution was prepared. First, a 1 mM buffer solution of 4-(2-hydroxyethyl)-piperazine-1-ethanesulfonic acid (HEPES) was prepared with a pH of 8.0 at 20° C. Second, a 30% w/w solution of acrylamide (AAM) in 1 mM HEPES buffer was prepared. Also, a 4% w/w solution of lithiumphenyl-2,4,6-trimethylbenzoylphosphinate (LAP) was prepared with the 1 mM HEPES buffer to be used as a photonitiator. Third, 19.1 mg of 3-acrylamidophenylboronic acid (3-APB) was dissolved in 87 μL of dimethyl sulfoxide and mixed with 237 μL of the 30% w/w AAM solution. Fourth, 193 μL of 2% w/w solution of N,N'-methylenebisacrylamide (BIS) along with 309 μL of 1 mM HEPES buffer and 20.48 μL of N-[3-(dimethylamino)propyl]methacrylamide was added to the mixture. Finally, 25.8 μL of the prepared photoinitiator was added in the dark to avoid crosslinking under normal light.

Polyimide (PI) polymer films of 25 μm thickness were used as substrates. They were surface-modified by placing them in a mixture of methanol, N-(3-aminopropyl)methacrylamide hydrochloride, and tributylamine and then in AAM, BIS, and HEPES buffer mixture. The functionalized PI films were used as the base layer where the pre-gel solution is crosslinked into the smart hydrogel by means of collimated UV light at 10 W power for 3.5 mins. Two hydrogel sheets of 140 μm and 280 μm thickness respectively were fabricated by means of varying the thickness of a PTFE spacer used between the polyimide and the glass cover. The hydrogel sheet and the underlying PI film were then cut into thin strips (length 1 cm, width 500 μm) using a tool made from two razor blades and a spacer. These strips were attached to a catheter tip (18 G) with cyanoacrylate-based adhesive. Finally, the assembly was subjected to a conditioning process to ensure reproducibility of the measurement results.

To image the sensor in a variety of concentrations of glucose solutions at 4 MHz, a medical ultrasound imaging module (ACUSON S2000, Siemens Medical Solutions USA, Inc.) with an ultrasound probe (9L4, Siemens Medical Solutions USA, Inc.) was used. The catheter was fixed inside a container containing the analyte solution, and the probe was fixed on top of the sensors at a focal distance of 3 cm. The imaging axis was along the length of the strip. The dynamic range was set to maximum. When the solution was changed, the container and the probe were first rinsed three times with the new solution. Solutions and sensors were kept at room temperature for 12 hours before any experiments to avoid temperature drift effects.

The glucose solutions used in this study were prepared by adding appropriate amount of 1× phosphate buffer solution (PBS) to 500 mM of glucose stock solution. For the stock solution 18.1 g of D-(+)-Glucose was dissolved in 170 mL of 1×PBS and then volume was increased to 200 mL by addition of PBS. PBS solutions used were prepared by dissolving 8 g of NaCl, 0.2 g of KCl, 0.24 g of $KH_2PO_4$, and 1.44 g of $Na_2HPO_4$, in 800 mL of deionized (DI) water, and then the pH was adjusted to 7.40 at 22° C. Finally, the volume was brought to 1 L by adding DI water.

For evaluation, the grayscale images were analyzed for their mean grayscale value in the hydrogel area. First, the images underwent a stabilization step. Next, a region of interest (ROI) was selected around the gel area with an area of 400 pixels (length=40 pixels, width=10 pixels). All the images were evaluated with the same ROI within one experiment. In the last step, all of the individual images' MGV (also referred to as mean pixel intensity, or MPI) were calculated and plotted with respect to time.

Figure 11:
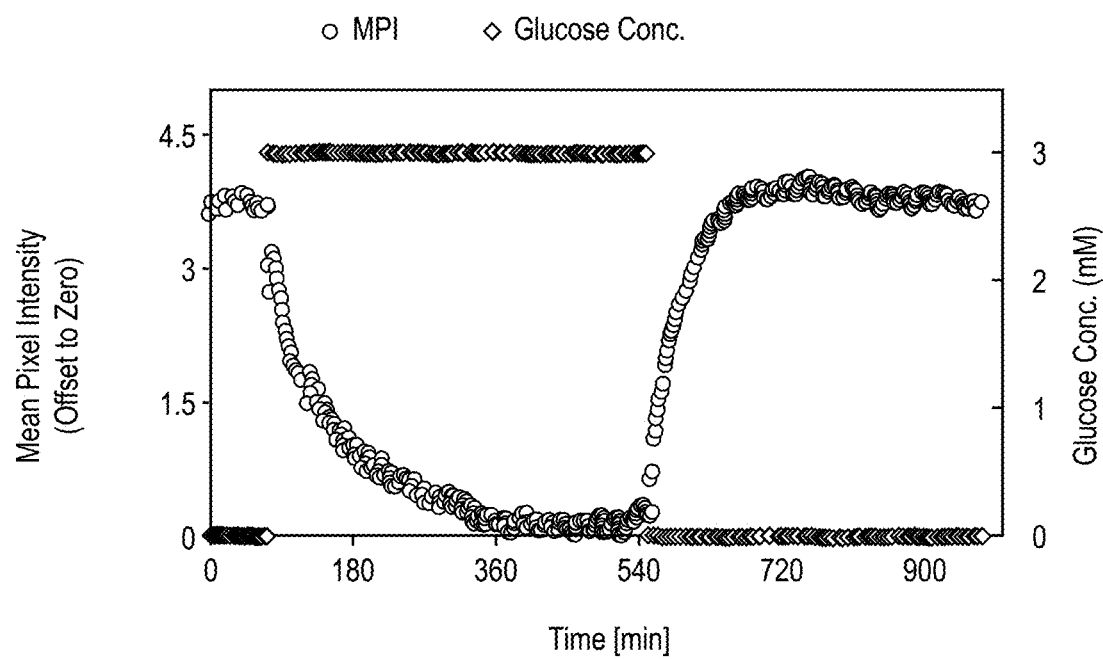
FIG. 11 shows MGV (or MPI) response over time for a smart hydrogel resonator structure on a catheter tip, with a hydrogel sheet thickness of 280 μm, queried at 4 MHz, when exposed to 0 mM and 3 mM glucose.
Figure 12:
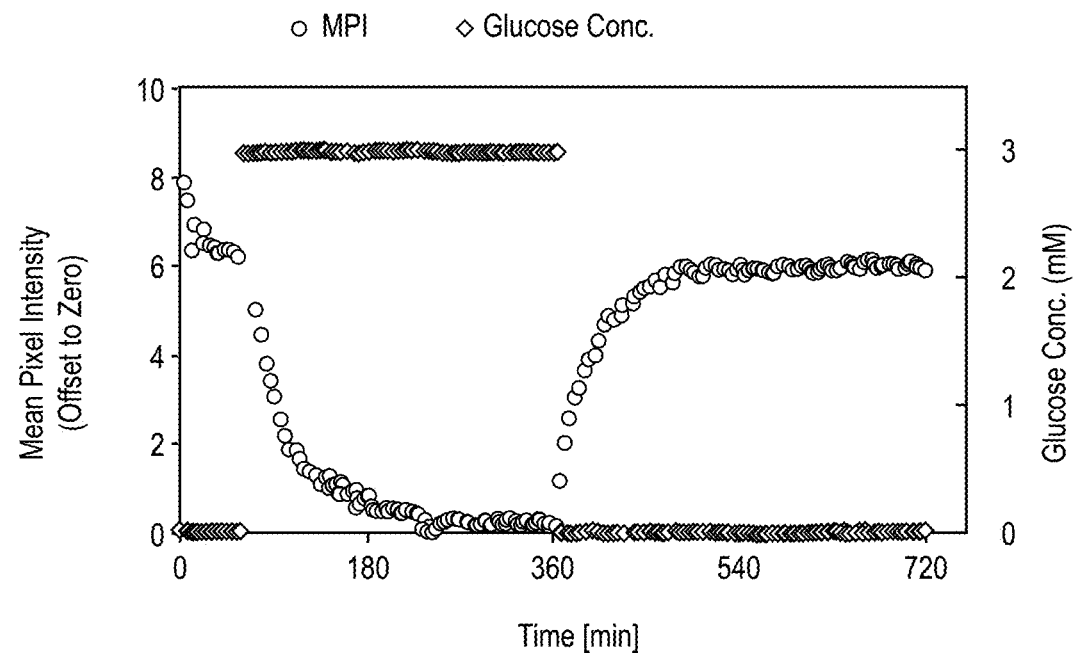
FIG. 12 shows MGV (or MPI) response over time for a smart hydrogel resonator structure on a catheter tip, with a hydrogel sheet thickness of 140 μm, queried at 4 MHz, when exposed to 0 mM and 3 mM glucose.

Two catheter tips with a hydrogel strip with thickness of 280 μm and 140 μm, respectively, were exposed to glucose concentrations of 3 mM to show the influence of hydrogel resonator thickness as exhibited in FIG. 11 and FIG. 12. For a 280 μm thick gel, the sensor was imaged in 1×PBS for one hour, and then, 3 mM of glucose solution was introduced, followed by continual imaging over 7 h. Finally, the sensor was exposed again to 1×PBS, and imaging continued for another 7 h. From FIG. 11, the T90 values are 104 min for swelling (3 mM to 0 mM of glucose) and 190 min for shrinking (0 mM to 3 mM of glucose). The T90 value represents the time span until 90% of the steady-state value is reached. For the catheter with a 140 μm thick gel, at first, the sensor was in 1×PBS for one hour, imaged, and subsequently, 3 mM of glucose was added, followed by continual imaging over 5 h. Finally, the sensor was exposed again to 1×PBS, and imaging continued for another 6 h. FIG. 12 shows the response of the sensor at 4 MHz frequency. The T90 values are 80 min for swelling (3 to 0 mM glucose) and 110 min for shrinking (0 to 3 mM of glucose).

Figure 13A:
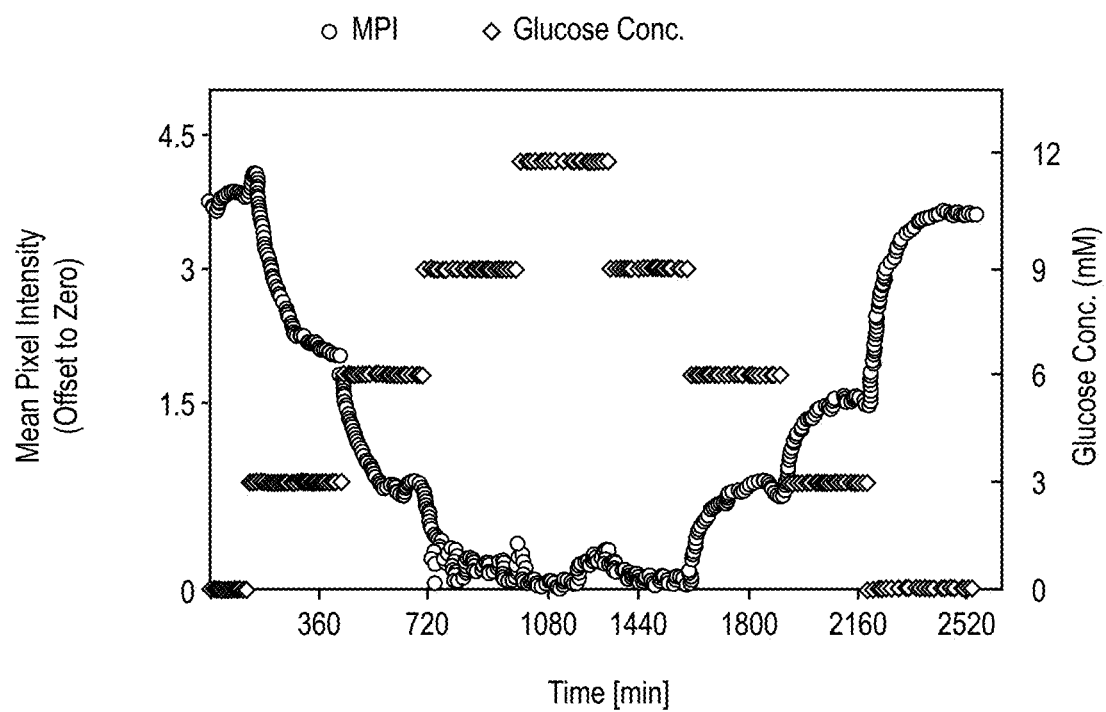
FIG. 13A shows MGV (or MPI) response over time for a smart hydrogel resonator structure on a catheter tip, with a hydrogel sheet thickness of 140 μm, queried at 4 MHz, when exposed to 0 mM to 12 mM glucose in 3 mM steps.
Figure 13B:
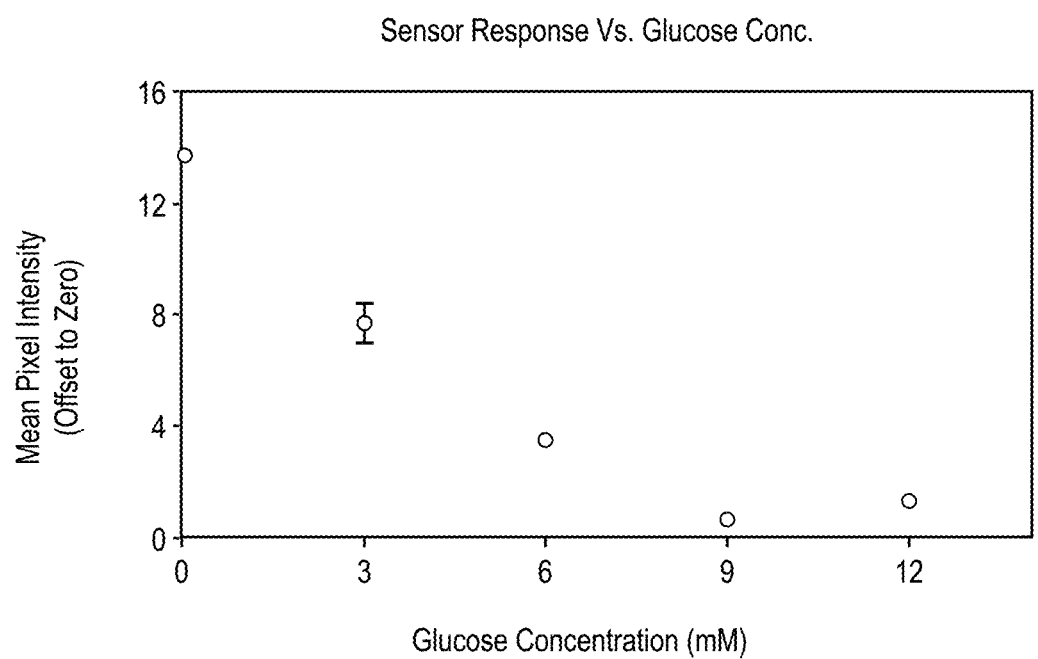
FIG. 13B shows MGV (or MPI) steady state values for each step averaged over the increasing and decreasing glucose concentration for the hydrogel sheet data of FIG. 13A.

For the second experiment, the sensor was introduced to glucose concentrations starting from 0 mM up to 12 mM in incremental steps of 3 mM. The concentration of glucose was then decreased from 12 mM glucose to 0 mM in the same steps. The time interval in-between steps was 5 h each, where the sensor was continuously imaged at 4 MHz. FIG. 13A shows the response of the sensor structure over time for these glucose concentrations. FIG. 13B shows the responses resulting from averaging the values obtained for each concentration, and the error bars show the standard deviation of those values.

The present example demonstrates proof-of-principle. The sensing system's applicability can easily be adapted to a variety of drugs or other analytes in the bloodstream or in another environment to be monitored by replacing the glucose-sensitive hydrogel with another smart hydrogel. The example shows successful miniaturization of the hydrogel sheet dimensions into a strip (length: 10 mm, width: 500 μm) configured to fit on the tip of a catheter (18 G, BD Insyte). In addition, by reducing the thickness to 140 μm from 280

µm, the T90 response time was reduced by almost ⅓, for glucose. The difference in the T90 response times is due to the difference in critical dimension between the two thicknesses of the gel, affecting the diffusion time. The response time of the smart hydrogel to glucose is within an expected range of 60 min to 175 min. Of course, response time may differ with different analytes due to different diffusion properties and binding mechanisms in the hydrogel. For example, glucose sensitivity is based on complex formation of glucose molecules with the boronic acid groups of the polymer network. In the case of anesthesia drugs such as fentanyl, however, the interaction with the polymer network may occur in a different way, e.g., by aptamer binding. From FIGS. 11-12 it can be seen that the sensors' sensitivity for glucose response is 1.2 MPI/mM (for 280 µm) and 2.2 MPI/mM (for 140 µm). Reasons for the smaller response magnitudes of the thicker gel may be due to differences in its resonance condition when excited at 4 MHz. FIGS. 13A-13B shows that MPI values decrease for increasing concentrations of glucose. However, for 12 mM glucose, the steady-state MPI is somewhat higher than 9 mM. Since high amounts of glucose in the solution leads to higher amounts of diols, each boronic acid group binds with more diols forming 1:1 complex bonds causing the gel to swell. This is different from regular 2:1 complex bonds that occur with lower amounts of glucose in solution that increases the crosslinks, causing the gel to shrink. The similar response magnitude between the start and the end of each experiment suggests that the sensor has a low hysteresis and is thus capable of reproducible measurements.

This example demonstrates fabrication of catheter-mounted smart hydrogel resonators useful as sensing components with remote readout via ultrasound. The obtained proof-of-principle results validate the potential of the sensing system. Future development could improve both response time and analyte sensitivity. While the example uses a glucose sensitive smart hydrogel, it will be apparent that such can be replaced by a smart hydrogel that is responsive to any other desired analyte. As such, the present catheter mounted smart hydrogel-based system can provide intravenous monitoring of clinically relevant analytes (e.g., anesthesia medications). Similarly, mounting could be to a substrate other than a catheter, e.g., depending on the particular environment being monitored.

While many of the illustrative embodiments for the present disclosure are described in the context of use of ultrasound to detect and/or measure an analyte concentration as a result of a change in resonance frequency characteristics of the smart hydrogel in an in vivo or other medical environment, it will be appreciated that the present methods using smart hydrogels having a resonance frequency and ultrasound query at or near such resonance frequency can also be used in a wide variety of other environments where it is desired to detect the presence and/or concentration of a given target analyte. For example, such methods and systems could be used in monitoring pipelines, or any hazardous or other environment, where one does not need to be concerned about seal failure often associated with monitoring in such environments.

Associated Computer Systems

Embodiments of the present invention may comprise or utilize a special purpose or general-purpose computer including computer hardware, as discussed in greater detail below, e.g., for calculation of MGV, calculation of resonance frequency, calculation of ultrasound wave or pulse intensity or amplitude, changes in any of such, or calculation of other relevant values. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

CONCLUSION

Any headings used herein are for organizational purposes only and are not meant to be used to limit the scope of the description or the claims.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively. Unless defined otherwise, all technical and scientific terms used herein have the same meaning as commonly understood by one of ordinary skill in the art to which the present disclosure pertains.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition.

Disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure. Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Accordingly, the present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

The invention claimed is:

1. A system for identifying one or more changes in a smart hydrogel microresonator structure positioned within an environment and having an acoustic resonance frequency in an ultrasound range, the system comprising:
   a smart hydrogel microresonator structure having an acoustic resonance frequency, the smart hydrogel microresonator structure being positioned within the environment and configured to exhibit a change in resonance frequency in response to interaction with one or more analytes in the environment, wherein the smart hydrogel microresonator structure is sufficiently unconstrained so as to be configured to resonate;
   an ultrasound transducer for querying the smart hydrogel microresonator structure within the environment at or near the acoustic resonance frequency of the smart hydrogel microresonator structure; and
   a computer system in communication with the ultrasound transducer, the computer system having one or more processors and being configured to:
      receive, from the ultrasound transducer, ultrasound data as provided by query of the smart hydrogel microresonator structure by the ultrasound transducer at or near the resonance frequency; and
      determine, at the one or more processors, at least one of: (i) a change in resonance frequency as induced by interaction of the one or more predefined analytes with the smart hydrogel microresonator structure in the environment; (ii) a change in mean grayscale value (MGV) associated with the ultrasound data of the smart hydrogel microresonator structure due to the change in the resonance frequency of the smart hydrogel microresonator structure as induced by interaction of the one or more predefined analytes with the smart hydrogel microresonator structure in the environment; or (iii) a change in amplitude or intensity of an ultrasound query wave or pulse as induced by interaction of the one or more predefined analytes with the smart hydrogel microresonator structure in the environment.

2. The system as in claim 1, wherein the ultrasound data is ultrasound image data, wherein the computer system is configured to determine the change in mean grayscale value (MGV) associated with the ultrasound image data of the smart hydrogel microresonator structure due to the change in the resonance frequency of the smart hydrogel microresonator structure as induced by interaction of the one or more predefined analytes with the smart hydrogel microresonator structure in the environment.

3. The system as in claim 1, wherein the computer system is configured to determine the change in resonance frequency of the smart hydrogel microresonator structure as induced by interaction of the one or more predefined analytes with the smart hydrogel microresonator structure in the environment.

4. The system as in claim 1, wherein the computer system is configured to determine the change in amplitude or intensity of an ultrasound query wave or pulse as induced by interaction of the one or more predefined analytes with the smart hydrogel microresonator structure in the environment.

5. The system as in claim 1, wherein the computer system receives, from the ultrasound transducer, the ultrasound data of the smart hydrogel microresonator structure at a first time and at a second time, and wherein the computer system determines, at the one or more processors, a change in MGV, change in resonance frequency, or change in amplitude or intensity of the ultrasound wave or pulse associated with the smart hydrogel microresonator structure based on differences in the ultrasound data of the smart hydrogel microresonator structure at the first time and at the second time.

6. The system as in claim 1, wherein the smart hydrogel microresonator structure does not include any markers, contrast agents, or external connections.

7. The system as in claim 1, wherein the smart hydrogel microresonator structure consists of a hydrogel material and optionally a polymer backplane.

8. The system as in claim 1, wherein the smart hydrogel microresonator structure is in the form of a sheet.

9. The system as in claim 1, wherein the smart hydrogel microresonator structure is in the form of one or more pillars, a backplane with one or more pillars extending therefrom, a dome, a pyramid, triangular prism, or a cube or other rectangular prism.

10. The system as in claim 1, wherein the smart hydrogel microresonator structure has a thickness from 100 μm to 1000 μm and is 0.1 mm to 20 mm in length.

11. The system as in claim 1, wherein the smart hydrogel microresonator structure is biodegradable in vivo.

12. The system as in claim 1, wherein the smart hydrogel microresonator structure is configured as a plurality of hydrogel microresonator pillars or other particles confined within a scaffold.

13. The system as in claim 1, wherein the system further comprises a control hydrogel positioned within the environment, the control hydrogel configured to not change resonance frequency in response to interaction with the one or more predefined analytes.

14. The system as in claim 1, wherein any change in dimension or volume of the smart hydrogel microresonator as a result of interaction with the one or more predefined analytes in the environment is not readily discernable in a generated ultrasound image.

15. The system as in claim 1, wherein the smart hydrogel microresonator structure is unconstrained to allow swelling or shrinking of the hydrogel in multiple dimensions.

16. The system as in claim 1, wherein the smart hydrogel microresonator structure is attached to a substrate.

17. A method for identifying one or more changes in a smart hydrogel microresonator structure positioned within an environment and having a resonance frequency in an ultrasound range, the method comprising:
providing a smart hydrogel microresonator structure, the smart hydrogel microresonator structure being positioned within the environment and configured to exhibit a change in resonance frequency in response to interaction with one or more predefined analytes in the environment, wherein the smart hydrogel microresonator structure is sufficiently unconstrained so as to be configured to resonate;
providing an ultrasound transducer for querying the smart hydrogel microresonator structure within the environment at or near the resonance frequency of the smart hydrogel microresonator structure;
providing a computer system in electrical communication with the ultrasound transducer, the computer system having one or more processors and being configured to:
receive, from the ultrasound transducer, ultrasound data as provided by query of the smart hydrogel microresonator structure by the ultrasound transducer at or near the resonance frequency; and
determine, at the one or more processors, at least one of: (i) a change in resonance frequency as induced by interaction of the one or more predefined analytes with the smart hydrogel microresonator structure in the environment; (ii) a change in mean grayscale value (MGV) associated with the ultrasound data of the smart hydrogel microresonator structure due to the change in the resonance frequency of the smart hydrogel microresonator structure as induced by interaction of the one or more predefined analytes with the smart hydrogel microresonator structure in the environment; or (iii) a change in amplitude or intensity of an ultrasound query wave or pulse as induced by interaction of the one or more predefined analytes with the smart hydrogel microresonator structure in the environment;
querying the smart hydrogel microresonator structure with the ultrasound transducer in the environment, at or near a resonance frequency of the smart hydrogel microresonator structure;
determining at least one of (i) the change in resonance frequency as induced by interaction of the one or more predefined analytes with the smart hydrogel microresonator structure in the environment; (ii) the change in mean grayscale value (MGV) associated with the ultrasound data of the smart hydrogel microresonator structure due to the change in the resonance frequency of the smart hydrogel microresonator structure as induced by interaction of the one or more predefined analytes with the smart hydrogel microresonator structure in the environment; or (iii) the change in amplitude or intensity of an ultrasound query wave or pulse as induced by interaction of the one or more predefined analytes with the smart hydrogel microresonator structure in the environment; and
determining the presence of and/or a concentration of one or more analytes based on the determination of (i), (ii) or (iii).

18. The method as in claim 17, wherein the computer system receives, from the ultrasound transducer, ultrasound data of the smart hydrogel microresonator structure at a first time and at a second time, and wherein the computer system determines, at the one or more processors, a change in MGV, a change in resonance frequency or a change in amplitude or intensity of the ultrasound query wave or pulse associated with the smart hydrogel microresonator structure based on differences in the ultrasound data from query of the smart hydrogel microresonator structure at the first time and at the second time.

19. The method as in claim 17, wherein the smart hydrogel microresonator structure consists of a hydrogel material and optionally a polymer backplane.

20. The method as in claim 17, wherein the smart hydrogel microresonator structure is in the form of one or more of (i) a sheet; (ii) a backplane with one or more pillars extending therefrom; (iii) a plurality of hydrogel microresonator pillars or other particles confined within a scaffold, or (iv) pillars free of a backplane, a dome, a pyramid, triangular prism, or a cube or other rectangular prism.

21. The method as in claim 17, wherein the smart hydrogel microresonator structure is biodegradable in vivo, the method further comprising allowing the smart hydrogel microresonator to biodegrade in vivo without retrieval thereof.

22. A detection system including an integrated smart hydrogel microresonator structure on a substrate for determining a concentration of an analyte in an environment adjacent to the substrate, the system comprising:
   a substrate having a tip;
   a smart hydrogel microresonator structure having a resonance frequency, positioned on the substrate tip, the smart hydrogel microresonator structure being positioned within a detection environment during use, and configured to exhibit a change in resonance frequency in response to interaction with a drug or other analyte in the detection environment, wherein the smart hydrogel microresonator structure is sufficiently unconstrained so as to be configured to resonate;
   an ultrasound transducer for querying the smart hydrogel microresonator structure within the detection environment at or near the resonance frequency of the smart hydrogel microresonator structure; and
   a computer system in electrical communication with the ultrasound transducer, the computer system having one or more processors and being configured to:
      receive, from the ultrasound transducer, ultrasound data as provided by query of the smart hydrogel microresonator structure by the ultrasound transducer at or near the resonance frequency; and
      determine, at the one or more processors, at least one of: (i) a change in resonance frequency as induced by interaction of the drug or other analyte with the smart hydrogel microresonator structure in the detection environment; (ii) a change in mean grayscale value (MGV) associated with the ultrasound data of the smart hydrogel microresonator structure due to the change in the resonance frequency of the smart hydrogel microresonator structure as induced by interaction of the drug or other analyte with the smart hydrogel microresonator structure in the detection environment; or (iii) a change in amplitude or intensity of an ultrasound query wave or pulse as induced by interaction of the one or more predefined analytes with the smart hydrogel microresonator structure in the detection environment.

* * * * *